United States Patent

Himeno et al.

Patent Number: 5,725,370
Date of Patent: Mar. 10, 1998

[54] DENTAL TIP

[75] Inventors: Hiroshi Himeno, Sapporo; Kazuko Himeno, 3-1-4, Tomioka 5-jo, Teine-ku, Sapporo-shi, Hokkaido; Kenichi Kita, Takarazuka; Tadashi Imanishi, Yokohama, all of Japan

[73] Assignees: Kazuko Himeno, Hokkaido; Takarazuki Plastic Industry Co., Ltd., Hyogo, both of Japan

[21] Appl. No.: 581,203

[22] Filed: Dec. 29, 1995

[30] Foreign Application Priority Data

Dec. 29, 1994 [JP] Japan .................... 6-339797

[51] Int. Cl.⁶ .................................... A61C 1/07
[52] U.S. Cl. ........................ 433/86; 433/80; 433/119
[58] Field of Search ........................ 433/80, 81, 86, 433/141, 118, 119, 165, 166

[56] References Cited

U.S. PATENT DOCUMENTS

| | | | |
|---|---|---|---|
| Re. 30,536 | 3/1981 | Perdreaux, Jr. | 433/86 |
| 3,842,632 | 10/1974 | Nelson | 433/165 X |
| 3,924,335 | 12/1975 | Balamuth et al. | 128/24 A |
| 4,038,571 | 7/1977 | Hellenkamp | |
| 4,735,200 | 4/1988 | Westerman | 128/66 |
| 4,832,683 | 5/1989 | Idemoto et al. | 433/119 X |
| 4,975,056 | 12/1990 | Eibofner | 433/165 |
| 5,096,421 | 3/1992 | Seney | 433/165 |
| 5,340,310 | 8/1994 | Bifulk | |
| 5,489,208 | 2/1996 | Mandell | 433/165 |
| 5,531,597 | 7/1996 | Foulkes et al. | 433/119 |

FOREIGN PATENT DOCUMENTS

| | | |
|---|---|---|
| 0015672 | 9/1980 | European Pat. Off. |
| 0496703 | 7/1992 | European Pat. Off. |
| 0565471 | 10/1993 | European Pat. Off. |
| 2659846 | 9/1991 | France |

Primary Examiner—Nicholas D. Lucchesi

[57] ABSTRACT

A dental tip comprises a proximal end portion connected to a drive source and a distal end portion adapted to act on a region to be subjected to dental treatment. The distal and proximal end portions are formed of a composite-material molded product which includes a plastic base material and an inorganic filler or/and an organic filler compounded therewith. This tip can produce the same treatment effect as a conventional one without damaging teeth or prostheses in dental treatment, and can be manufactured with ease. Thus, the tip is low-priced and disposable.

21 Claims, 13 Drawing Sheets

DENTAL TIP

BACKGROUND OF THE INVENTION

1. Field of the Invention

The present invention relates to a dental tip adapted for use in periodontal treatment or endodontics which utilizes ultrasonic vibration, and more specifically, to a dental tip which can remove calculus (dental calculus) and other deposits without damaging teeth, prostheses, implants, etc., can be manufactured with ease, and is disposable, and a method for manufacturing the same, and moreover, to a dental tip in which irrigating water or a chemical agent can be efficiently fed to its distal end portion during dental treatment.

2. Description of the Related Art

Calculus and plaque (bacterial dental plaque) constitute the primary causes of periodontal disease and dental caries. For treatment and prevention of dental diseases, therefore, it is essential to remove those calculus and plaque which adhere to the surfaces of teeth or root surfaces.

In such treatment, there are important basic procedures including removal of calculus from the tooth surfaces, debridement in pockets, and detoxification or glossing of root surfaces, that is, scaling or root planing.

The scaling is an operation for removing deposits, such as plaque, calculus, of subgingiva. The root planing is an operation for glossing the root surfaces and removing residual calculus on the root surfaces, subgingival calculus, necrosed cementum, etc., thereby detoxifying the root surfaces.

Normally, the scaling and root planing operations are performed by using a manual scaler, especially a manual metallic curette type scaler. Presently, this is believed to be the securest method in the world. The scaling and root planing operations by means of the manual curette scaler, however, require a great deal of skill and take much time and labor.

In some cases, the scaling and root planing may be carried out by supplementally using a rotosonic scaler for engine, air scaler for turbine, ultrasonic scaler, etc. instead of using the manual scaler.

The rotosonic scaler for engine is a treatment appliance which is designed so that a rotating tip in the form of a hexagonal pyramid, for example, is attached to its distal end, and the tip is held against calculus or the like as it is rotated, thereby grinding and removing the calculus or other deposits. The air scaler for turbine is a treatment appliance which is designed so that an exclusive-use tip in the form of a metallic rod, for example, is held against calculus as it is rotated or vibrated by utilizing a high-speed rotary motion of an air turbine, thereby grinding and removing the calculus or other deposits.

In the ultrasonic scaler, on the other hand, an exclusive-use metallic tip having a complicated shape fit for the surface of a tooth is connected to an ultrasonic vibration source, and ultrasonic vibration is transmitted to the distal end of the tip by vibrating the vibration source in the ultrasonic zone.

The distal end of the tip, thus subjected to the ultrasonic vibration, is held against calculus or the like which adhere to the tooth surface, thereby grinding and removing them to gloss the tooth surface. In general, these appliances produce great vibration, and are liable to damage the tooth surface. Also, their vibration and noises give patients an unpleasant feeling, and therefore, an unfavorable impression.

Described in Jpn. Pat. Appln. KOKAI Publication No. 5-154164 is a novel, improved ultrasonic scaler which can grind and remove calculus and the like with the output power of the vibration source restrained lest the gingiva or other soft tissue be injured when the calculus and the like, adhering to the root surface and hidden under the gingiva, are ground.

In this ultrasonic scaler, as shown in FIG. 1, a tip 1 having a complicated shape, curved three-dimensionally so as to fit the tooth surface or root surface, is connected to a hand piece 2 for use as an ultrasonic vibration source. Ultrasonic vibration is transmitted to the distal end portion of the tip 1 by vibrating a drive source in the hand piece 2 in the ultrasonic zone. The distal end portion of the tip 1, thus resonated, is held against the region to be treated, thereby grinding and removing calculus or the like. In the case of this ultrasonic scaler, therefore, the amplitude of vibration of the distal end of the tip can be augmented and stabilized even though supplied ultrasonic energy is very low, and the ultrasonic vibration can be utilized effectively. Thus, the removal of the calculus on the root surface and other procedures can be efficiently carried out without damaging the gingiva or other soft tissue.

Generally, moreover, the ultrasonic scaler can be also used for root canal treatment if the tip is replaced with an exclusive one therefor or a file.

The root canal treatment mentioned herein includes procedures such as root canal enlargement, removal of soft tissue or necrosed tissue from the root canal, preparation of root canal and root canal irrigation, root canal filling, etc., and reversed root canal treatment in which the same procedures are reversely carried out involving operation.

In order to execute the above procedures efficiently, distilled water or tap water, as irrigating water, or a chemical agent is supplied from the distal end of the tip 1 to the region to be treated. To attain this, the irrigating water or chemical agent is fed to the region to be treated through a liquid supply port 2a at the proximal end side of the hand piece 2 and a liquid passage 1a in the tip 1, as shown in FIGS. 1 and 2.

Conventionally, the manual curette scaler has widely been used in the scaling and root planing treatment, as mentioned before. Recently, however, the rotosonic scaler, which rotates or vibrates the tip mechanically, air scaler, ultrasonic scaler, etc. have started to be generally used for the treatment and prevention of dental diseases. With these appliances, scaling, root planing, root canal treatment, etc. can be carried out relatively easily and efficiently.

Usually, dental tips which are attached to the rotosonic scaler, air scaler, ultrasonic scaler, etc. are made of a metal material, such as stainless steel, which is highly resistant to corrosion and wear. The metallic dental tips, hard enough, are not very susceptible to wear during use, and can efficiently remove calculus or other deposits in a short time, so that they are highly available for dental treatment.

However, the metallic dental tips are so much harder than teeth or artificial restorative materials (hereinafter referred to as prostheses), such as implanted artificial roots, artificial teeth, inlays, amalgam, etc., that they are liable to damage teeth or prostheses by only touching them.

If teeth or prostheses are damaged, calculus or plaque easily adhere to their damaged regions, newly causing dental caries or periodontal disease.

Since the damaged surfaces of teeth or prostheses spoil the intraoral sanitary conditions, it is advisable to minimize the incidence of such damage in dental treatment.

However, the metallic dental tips are too much harder than teeth or prostheses to fulfill the above requirement.

Dental tips for ultrasonic scaling or root planing have a complicated shape, curved three-dimensionally so as to fit the tooth surface or root surface, and are provided with a tubule for the passage of irrigating water. Accordingly, the manufacture of these tips require skillful manual operations, so that the tips cannot be mass-produced with ease. Inevitably, therefore, the dental tips of this type are expensive.

In order to avoid infection with highly infectious diseases, such as serum hepatitis, AIDS, etc., during dental treatment in these days, treatment appliances, especially ones adapted to be directly in contact with secretions, such as saliva, blood, etc., and/or having a tubule are expected to be disposable. Since the metallic dental tips are very expensive, as mentioned before, however, they cannot be easily thrown away after being used only once in dental treatment.

In order to feed the irrigating water or chemical agent smoothly to the desired region to be treated, moreover, it is advisable to form the liquid passage $1a$ in the tip 1 so that it extends as close to the distal end $1b$ of the tip as possible. Due to various restrictions on the manufacture of the tip, however, it is very difficult to make the liquid passage extend to the thin distal end of the tip which has a complicated three-dimensional shape.

In manufacturing a metallic tip, for example, the liquid passage is first formed in a rod material by using a drill or the like, and the material is then shaped into a curved form by heat forging or bending. During this shaping operation, however, the drilled liquid passage may be closed, or the thin distal end portion of the tip may crack, for example. Thus, it is very hard to form the liquid passage so as to cover the distal end of the tip.

Inevitably, therefore, the conventional dental tips are designed so that the liquid passage $1a$ for irrigating water and the like is formed in a straight part of a proximal end portion $1c$ of the tip and opens in an intermediate portion $1d$ between the distal and proximal end portions $1b$ and $1c$ of the tip. These tips are subject to a drawback that the irrigating water or chemical agent ejected from an opening $1e$ leaves the tip and scatters, thus failing to reach the distal end portion $1b$, that is, to be satisfactorily fed to the ground surface or other region to be treated, if the ejection speed is too high.

In order to solve this problem, it is believed to be advisable to form a longitudinal groove along the curved outer surface of the tip 1 so that it extends from the opening $1e$ to the distal end portion $1b$ of the tip, for example. Practically, however, the formation of the longitudinal groove entails a substantial change in the vibration characteristics of the tip 1 such that the tip ceases to resonate with a predetermined oscillation frequency of the ultrasonic vibration source.

SUMMARY OF THE INVENTION

An object of the present invention is to provide a dental tip, which can produce the same treatment effect as the conventional metallic ones, without damaging teeth or prostheses in periodontal treatment or endodontics utilizing ultrasonic vibration, and can be manufactured with ease, so that the tip is low-priced and disposable, and a method for manufacturing the same.

Another object of the invention is to provide a dental tip, in which irrigating water or a chemical agent can be securely fed to its distal end portion without regard to the material of the tip during dental treatment, so that the efficiency of irrigation and treating affected regions to be treated can be improved.

In order to achieve above object, according to the present invention, there is provided a dental tip (hereinafter referred to as dental tip A) which comprises a distal end portion having a desired curved shape and adapted to act on a region to be subjected to dental treatment, and a proximal end portion connected to a drive source, the distal and proximal end portions being formed of a composite-material molded product including a plastic base material and an inorganic filler or/and an organic filler compounded therewith.

According to the invention, moreover, there is provided a method for manufacturing the dental tip A, which comprises a process for preparing two composite materials with different compositions by mixing a plastic base material with an inorganic filler or/and an organic filler, a process for fabricating a plurality of molded products by mixing the two composite materials in different mixture ratios and measuring the respective natural frequencies of the molded products, thereby seizing the correlation between the natural frequencies and the mixture ratios, a process for settling the mixture ratio between the two composite materials exhibiting a target natural frequency in accordance with the seized correlation, and a process for mixing the two composite materials in the settled mixture ratio, thereby forming a composite-material molded product.

According to the invention, furthermore, there is provided a dental tip (hereinafter referred to as dental tip B) which comprises a distal end portion having a desired curved shape and adapted to act on a region to be subjected to dental treatment, a proximal end portion connected to a drive source, a liquid passage having an opening in an intermediate portion between the distal and proximal end portions such that a liquid supplied from the proximal end side is jetted from the opening, and a cross groove formed close to the opening in the outer wall of the intermediate portion and extending substantially at right angles to the axis of the liquid passage.

The dental treatment mentioned herein relates to periodontal treatment or/and endodontics, and more specifically, to procedures for treatment or preventing dental diseases. These treatments or procedures include, for example, removal of deposits, grinding of affected regions, surface polishing, irrigating, root canal treatment, etc. for teeth or prostheses (hereinafter referred to generally as region(s) to be treated according to the invention). Preferably, therefore, the distal end portion of the dental tip according to the invention has a shape adapted for use in the aforesaid treatments or procedures. Thus, available tips include tips used with a rotosonic scaler or air scaler, tips having complicated shapes fit for the surface of a tooth, such as the ones used for scaling by means of an ultrasonic scaler and root planing, tips used in root canal treatment (root canal filling, root canal enlargement, or irrigating), etc.

DETAILED DESCRIPTION OF THE INVENTION

Dental tips A according to the present invention will be described first.

Figure 3:
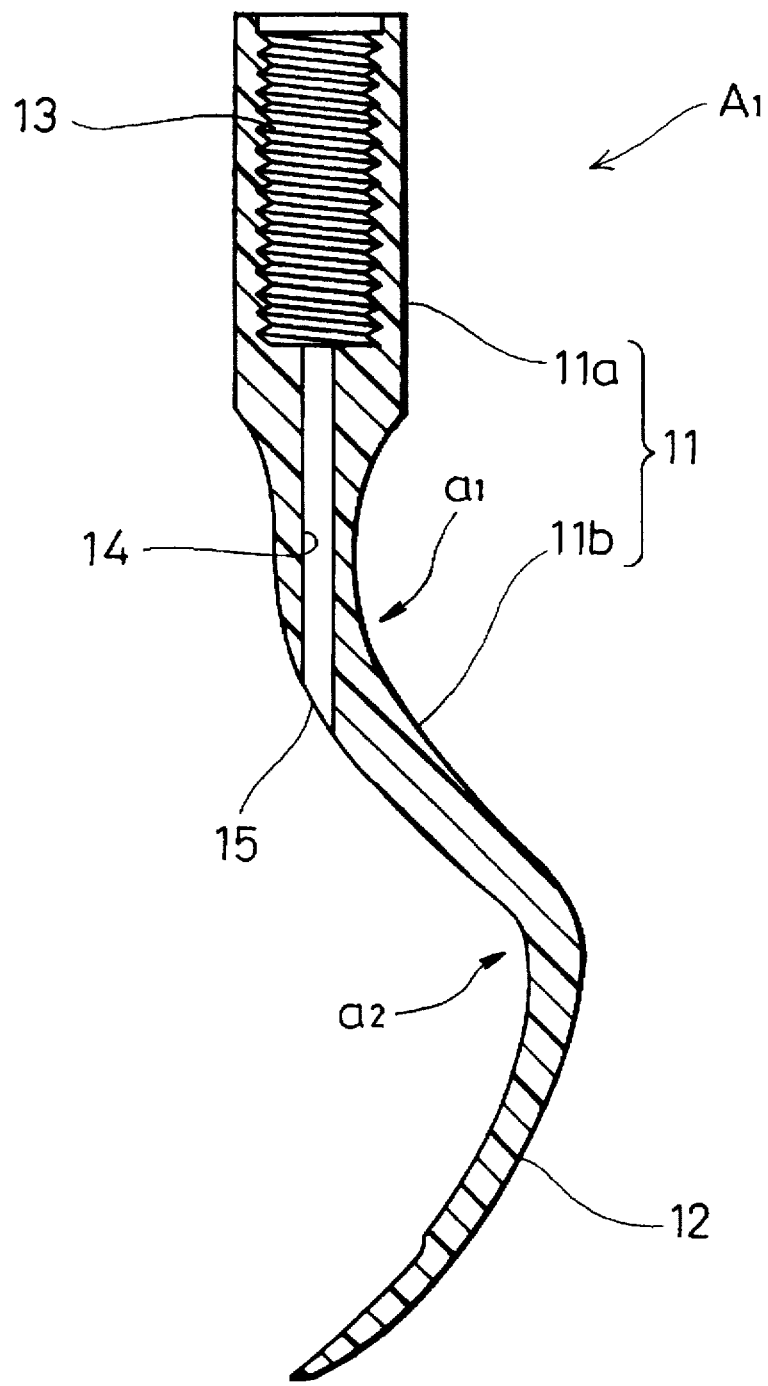
FIG. 3 is a sectional view showing a dental tip $A_1$ according to the present invention.

FIG. 3 is a sectional view showing an example $A_1$ of the dental tips A.

The dental tip $A_1$, which is adapted to be attached to an ultrasonic scaler, is an integral molded product having a proximal end portion 11 and a distal end portion 12.

The proximal end portion 11 includes a connecting portion 11a to be connected to a drive source and a support portion 11b. The connecting portion 11a extends straight along the axis of the proximal end portion 11, while the support portion 11b bends in a region $a_1$ in one direction with respect to the connecting portion 11a. The distal end portion 12 further bends in a region $a_2$ with respect to the support portion 11b, and has an intricate shape delicately curved back and forth and from side to side so that it can fit a complicated root surface and a root branch portion or root canal which cannot be observed directly from the outside. Thus, the dental tip $A_1$ is curved three-dimensionally and tapered from the proximal end portion 11 toward the distal end portion 12 as a whole.

In the proximal end portion 11 as defined herein, the connecting portion 11a is the basal part of the whole tip which serves to connect the tip to the drive source (not shown). The support portion 11b is an intermediate portion which is situated between the curved tapered distal end portion 12 and the connecting portion 11a, and supports the taped distal end portion 12.

Figure 2:
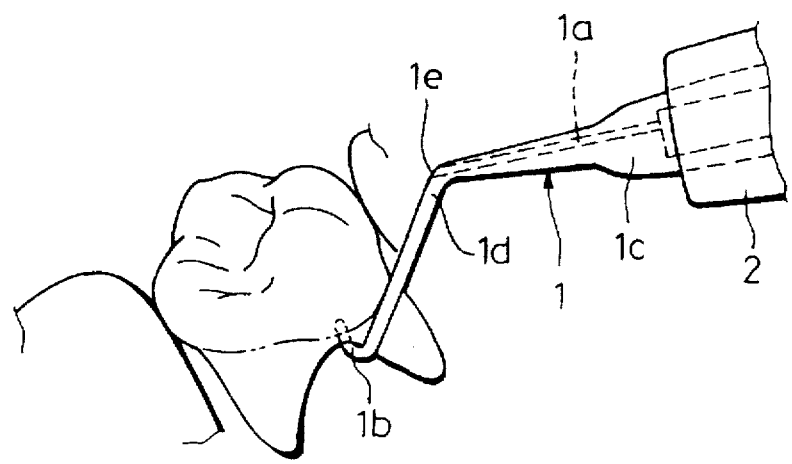
FIG. 2 is a partial perspective view showing a state of treatment conducted by means of the dental tip.

For example, a bottomed female screw 13 is cut to a desired depth in the connecting portion 11a. The dental tip $A_1$ can be attached to a hand piece 2 for use as an ultrasonic vibration source, as shown in FIG. 2, by screwing a male screw, as a connecting portion of the hand piece, into the female screw 13.

A liquid passage 14, having an opening 15 at one end thereof, extends from the bottom of the female screw 13 along the axis of the support portion 11b. Irrigating water (or chemical agent) fed through the liquid passage 14 can be jetted from the opening 15 to be sprayed on the distal end portion 12.

The dental tip $A_1$ is a composite-material molded product which is composed of a plastic base material (mentioned later) as a matrix and an inorganic filler or/and an organic filler (mentioned later) as a reinforcing material or materials.

A preferred example of the plastic base material used may be at least one material selected from a group including polyphenylene sulfide, polyamide, polyethylene terephthalate, polybutylene terephthalate, liquid crystal polymer, polycarbonate, polyether-ether ketone, polyether ketone, polyether sulfone, polysulfone, polyetherimide, polyamideimide, polyimide, and polyacetal.

Among these materials, polyphenylene sulfide is high in corrosion resistance, heat resistance (resistance of the composite-material molded product to temperatures as high as about 260° C.), and chemical resistance, and is nontoxic. Thus, the dental tip $A_1$, which is fabricated with use of polyphenylene sulfide for its matrix, can be safely used in the mouth or in the operation without changing its properties despite the contact with saliva in the oral cavity. Moreover, this dental tip can suitably enjoy sterilization by autoclave, boiling, chemical disinfection, etc.

The fillers compounded with the plastic base material are available as organic or inorganic ones. Also, they may be combinations of organic and inorganic fillers.

The organic or inorganic filler may be in the form of powder or a fiber. Alternatively, the inorganic filler may be in the form of whiskers. Relatively long filaments of the fibrous filler are cut into shorter filaments of suitable lengths.

Available inorganic fillers include, for example, a carbon fiber, fibrous potassium titanate, glass fiber, alumina fiber, titanium oxide, boron, talc, etc. The carbon fiber and fibrous potassium titanate are preferred in particular. These materials may be used independently or mixed suitably with one another.

For the organic filler, materials that do not melt at a molding temperature applied during the formation of the composite-material molded product are used, and a preferred example is aramide (aromatic polyamide) fibers.

As shown in FIG. 2, the dental tip $A_1$ is attached to an ultrasonic vibration source (drive source), such as the hand piece 2, when it is actually used. Preferably, in this case, vibration energy supplied from the ultrasonic vibration source is damped little, and the dental tip $A_1$ has a natural frequency such that it can resonate with the oscillation frequency supplied from the ultrasonic vibration source, in order that an effective vibration can be obtained even though the output power of the aforesaid drive source is low.

Even if the natural frequency of the dental tip $A_1$ is somewhat deviated from the frequency of the ultrasonic vibration source, however, the dental tip is practicable enough as long as an available vibration for the removal of calculus and the like can be transmitted substantially to the distal end portion of the tip.

More specifically, the dental tip is practicable if there are relations:

$$f-500 \text{ (Hz)} \leq f^o \leq f+500 \text{ (Hz)},$$

where f and $f_O$ are the oscillation frequency of the ultrasonic vibration source and the natural frequency of the dental tip.

In order to make the dental tip $A_1$ resonate in the vicinity of the oscillation frequency of the ultrasonic vibration source, as mentioned before, the following four items or factors should be examined. Preferably, these factors are combined so that the natural frequency of the tip is close to the oscillation frequency of the ultrasonic vibration source (with allowances of 500 Hz).

The materials of the composite-material molded product will be examined as a first factor.

Preferably, the composite-material molded product in the form of a dental tip is made of materials whose vibration can be damped little and whose natural frequency (resonance frequency) is resonant with the oscillation frequency of the ultrasonic vibration source.

If the materials of the composite-material molded product are too soft, in this case, the product cannot enjoy a desired or target resonance frequency, and the vibration energy supplied from the drive source is damped so much that ultrasonic vibration cannot be easily transmitted to the distal end portion 12 of the tip. If the materials are too hard, in contrast with this, the tip may possibly damage an affected region to be treated, and is liable to fracture.

Preferably, therefore, the composite-material molded product should be formed of materials such that it can resonate with the oscillation frequency of the ultrasonic vibration source to transmit its ultrasonic vibration securely to the distal end portion, and never damages the region to be treated. Thus, the composite-material molded product must necessarily have appropriate hardness and elasticity.

More specifically, the hardness of the composite-material molded product should be within the range of 65 to 120 in terms of the Rockwell hardness (M scale). If the Rockwell hardness is lower than 65, the supplied vibration energy is damped considerably. If the hardness is higher than 120, the molded product is liable to damage the region to be treated and fracture.

Preferably, the flexural modulus of elasticity of the composite-material molded product ranges form 2,500 to 25,000 MPa. If the flexural modulus is lower than 2,500 MPa, the transmissibility of the supplied ultrasonic vibration is too low to produce a satisfactory treatment effect. If the modulus is higher than 25,000 MPa, on the other hand, the tip is liable to fracture.

Further preferably, the Rockwell hardness (M scale) ranges from 75 to 100, and the flexural modulus of elasticity ranges from 10,000 to 25,000 MPa.

The aforesaid hardness and flexural modulus of the composite-material molded product or the transmissibility of the vibration energy supplied from the ultrasonic vibration source to the distal end portion of the tip, may vary depending on the kinds and formulations of the plastic base material and the filler used. If the filler is powder, for example, these conditions change also depending on the particle size of the powder. If the filler is formed of short filaments, the conditions change also depending on the diameter and aspect ratio of the filaments. Thus, the composite-material molded product, having the hardness and flexural modulus in the aforesaid ranges, can be manufactured by appropriately combining these conditions.

In this case, the functions of the composite-material molded product obtained as a dental tip vary depending on the kind of the filler, organic or inorganic.

In general, as the vibration energy propagating through the organic substance is liable to be absorbed, the damping capacity of vibration energy supplied to an organic substance increases. Accordingly, a composite-material molded product which is manufactured using the organic substance as a reinforcing material (filler) has a tendency toward an increase in the damping capacity of vibration energy. If the output power of the ultrasonic vibration source, fitted with the dental tip which is formed of the composite-material molded product, is lowered, therefore, the vibration energy supplied from the vibration source is inevitably damped before it reaches the distal end portion of the tip. In some cases, after all, the distal end portion of the dental tip may fail to resonate and produce a treatment effect.

Thus, the output power of the ultrasonic vibration source must be augmented in actually using the dental tips A of the composite-material molded product compounded with an organic filler, according to the present invention. An essential feature of the organic filler is that it has low wear resistance and cannot easily damage the region to be treated. So, the organic filler is important as the filler used in the present invention.

The aforesaid problem can hardly be aroused in the case where the composite-material molded product is compounded with an inorganic filler.

Even if the output power of the ultrasonic vibration source is lowered, therefore, the dental tips A of the present invention which are formed of a composite- material molded product compounded with an inorganic filler can perform an effective dental treatment.

The combination and formulation of the plastic base material and the filler are selected properly in consideration of these circumstances.

In the case of a composite-material molded product whose plastic base material and filler are formed of, for example, polyphenylene sulfide and a carbon fiber, respectively, the carbon fiber loading preferably ranges from 10 to 50% by weight (therefore, the polyphenylene sulfide loading ranges from 50 to 90% by weight), further preferably from 20 to 40%. If the carbon fiber loading is less than 10% by weight, the aforementioned appropriate hardness cannot be obtained, and the vibration is damped considerably. If the carbon fiber loading is more than 50% by weight, on the other hand, the hardness and rigidity are so high that the tip easily fractures during use.

If the diameter and aspect ratio of the filaments of the carbon fiber used in the composite-material molded product is 7 to 9 μm and 15 to 100, respectively, the Rockwell hardness (M scale) of the resulting composite-material molded product ranges from 80 to 100, and the flexural modulus of elasticity ranges from 8,000 to 20,000 MPa. Even in the case where the output power of the ultrasonic vibration source is low, therefore, the transmissibility of the ultrasonic vibration is enhanced, and the composite-material molded product with a desired natural frequency can be manufactured with ease.

In the case of a composite-material molded product in which polyphenylene sulfide as the plastic base material is compounded with 10 to 50% by weight of fibrous potassium titanate as the filler, the diameter and aspect ratio of the filaments of the fibrous filler may range from 0.3 to 0.6 μm and from 15 to 67, respectively. In this case, the Rockwell hardness (M scale) ranges from 80 to 100, and the flexural modulus-of elasticity ranges from 5,000 to 15,000 MPa, both enjoying appropriate figures. Even in the case where the output power of the ultrasonic vibration source is low, therefore, the transmissibility of the ultrasonic vibration is enhanced favorably.

In the case of a composite-material molded product in which aforesaid composite-material molded product is further compounded with about 5% by weight of an aramide fiber as the filler having a filament diameter of 12 μm, the Rockwell hardness (M scale) and the flexural modulus of elasticity ranges are 75 and 7,000 MPa, respectively. In this case, the transmissibility of the ultrasonic vibration is supposed to be lower than in the cases of the aforesaid two composite-material molded products. Thus, when actually using this composite-material molded product as a dental tip, it must be actuated by means of an ultrasonic vibration source with a higher output power than in the case of the product compounded with the aforesaid inorganic filler.

The shape of the dental tip itself will be examined as a second factor.

Even though formed of composite-material molded products of the same composition, tips having different shapes resonate in different ways when they are attached to the same ultrasonic vibration source and operated in the same conditions.

In the case of the tip $A_1$ shown in FIG. 3, for example, the natural frequency of the composite-material molded product of the same composition changes if the overall length of the tip or the curved shape of the distal end portion 12 is changed.

Preferably, therefore, the tip should have a shape such that it can resonate with the oscillation frequency of the ultrasonic vibration source, in order to produce a satisfactory ultrasonic vibration for a treatment effect at its distal end portion. In this case, it is essential to examine a shape for the satisfactory ultrasonic vibration in advance in an initial stage of design. Since the dental tip according to the present invention has its matrix formed of a soft plastic base material, it can be shaved easily, and its natural frequency can be finely adjusted by, for example, slightly shaving its proximal end portion to modify the overall shape after the tip is manufactured having a predetermined shape.

A third factor is a problem associated with the connection between the dental tip and the ultrasonic vibration source.

If this connection is secured, the vibration energy from the ultrasonic vibration source can be efficiently transmitted to the dental tip without being reflected or damped by the junction between the source and the tip.

It is advisable, therefore, to make a satisfactory connection with the ultrasonic vibration source, thereby preventing the vibration from being reflected or damped by the junction. According to a preferred method of connection, the dental tip is screwed to the ultrasonic vibration source with use of the female screw 13 cut in the proximal end portion 11, as shown in FIG. 3.

Figure 4:
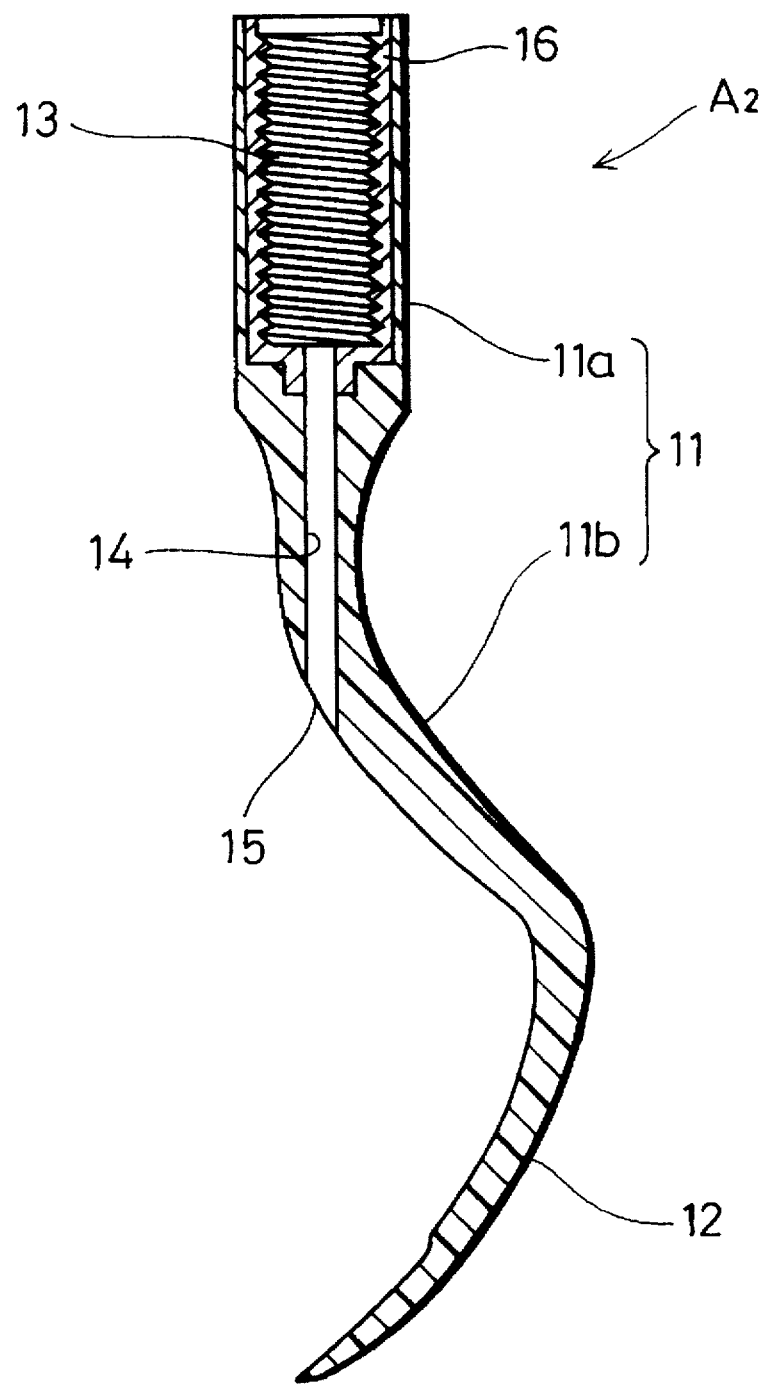
FIG. 4 is a sectional view showing another dental tip $A_2$ according to the invention.

In a dental tip $A_2$ of the present invention shown in FIG. 4, an open-topped metallic member 16, having a small hole at the bottom which communicates with the liquid passage 14, is embedded in the connecting portion 11a of the proximal end portion 11, and the female screw 13 is cut in the inner surface of the member 16. This arrangement ensures the satisfactory connection with the ultrasonic vibration source.

Instead of using the arrangement shown in FIG. 4, the female screw portion shown in FIG. 3 may, for example, be electrolessly plated so that the surface of the female screw 13 is coated with a predetermined metal. Alternatively, the screw-jointed portion may be tightly bound with a metal band. In this case, causes of damping of the ultrasonic vibration can be reduced by minimizing the number of junctions so that the whole structure is integral. Although adapters may be interposed in the middle, they may possibly constitute a cause of instability.

A fourth factor is a problem associated with the natural frequency of the whole system including the dental tip attached to the ultrasonic vibration source.

In order to establish a satisfactory state of resonance at the distal end portion of the tip in this system, it is essential that the natural frequency of the whole system including the ultrasonic vibration source, as well as that of the tip, be appropriate. This can be attained by examining the tip and the ultrasonic vibration source as an integral body for transmitting the vibration energy.

According to the dental tip of the present invention, moreover, the polishing effect of the distal end portion for the affected region to be treated can be improved in the following manner.

First, the matrix base material is compounded with an abrasive substance, besides the aforesaid filler, so that the abrasive substance is included and uniformly dispersed in the composite-material molded product or is attached in the form of a film on the surface of the molded product formed of the plastic base material and the filler.

In the case of a composite-material molded product manufactured by the former method, the abrasive substance is uniformly dispersed in the tip. Even though the distal end portion wears with treatment time as it grinds the region to be treated during actual use, therefore, the abrasive substance never fails to exist on the surface of the worn distal end portion, so that the polishing effect never lowers, that is, a desired polishing effect can be maintained at all times.

In the case of a composite-material molded product manufactured by the latter method, the filmy abrasive substance covering its surface (surface of the distal end portion) produces a polishing effect for the region to be treated. In this case, the abrasive substance is deposited by a conventional filming technique, such as coating, vapor deposition, or ion plating.

According to the latter method, the tip ceases to produce the polishing effect when its filmy abrasive substance is worn out. According to the former method, however, the tip can continue to produce the polishing effect before it is worn out entire. Accordingly, this tip can be also suitably applied to the case where regions in complicated shapes must be formed to effect the dental treatment and preventive operation.

The abrasive substance for this purpose may be any material which can produce a polishing effect for the region to be treated. Available abrasive substances include, for example, alumina, silica, glass, zirconia, silicon carbide, boron carbide, diamond, etc. Alumina is preferred in particular. These materials may be used independently or in combination with one another.

In the case where the abrasive substance to be uniformly dispersed together with the filler into the plastic base material is alumina, too fine particles cannot be uniformly dispersed into the base material with ease, while too coarse particles make the surface of the dental tip so rough that the tip will not polish but damage the region to be treated. Preferably, therefore, the particle size of the abrasive substance (alumina) ranges from about 1 to 50 μm. If the abrasive substance loading is too low, the polishing effect is lowered. If the loading is too high, in contrast with this, the hardness and flexural modulus of the composite-material molded product and the transmissibility of the vibration energy are adversely affected. Preferably, thereby, the abrasive substance loading ranges from 5 to 20% by volume.

Figure 5:
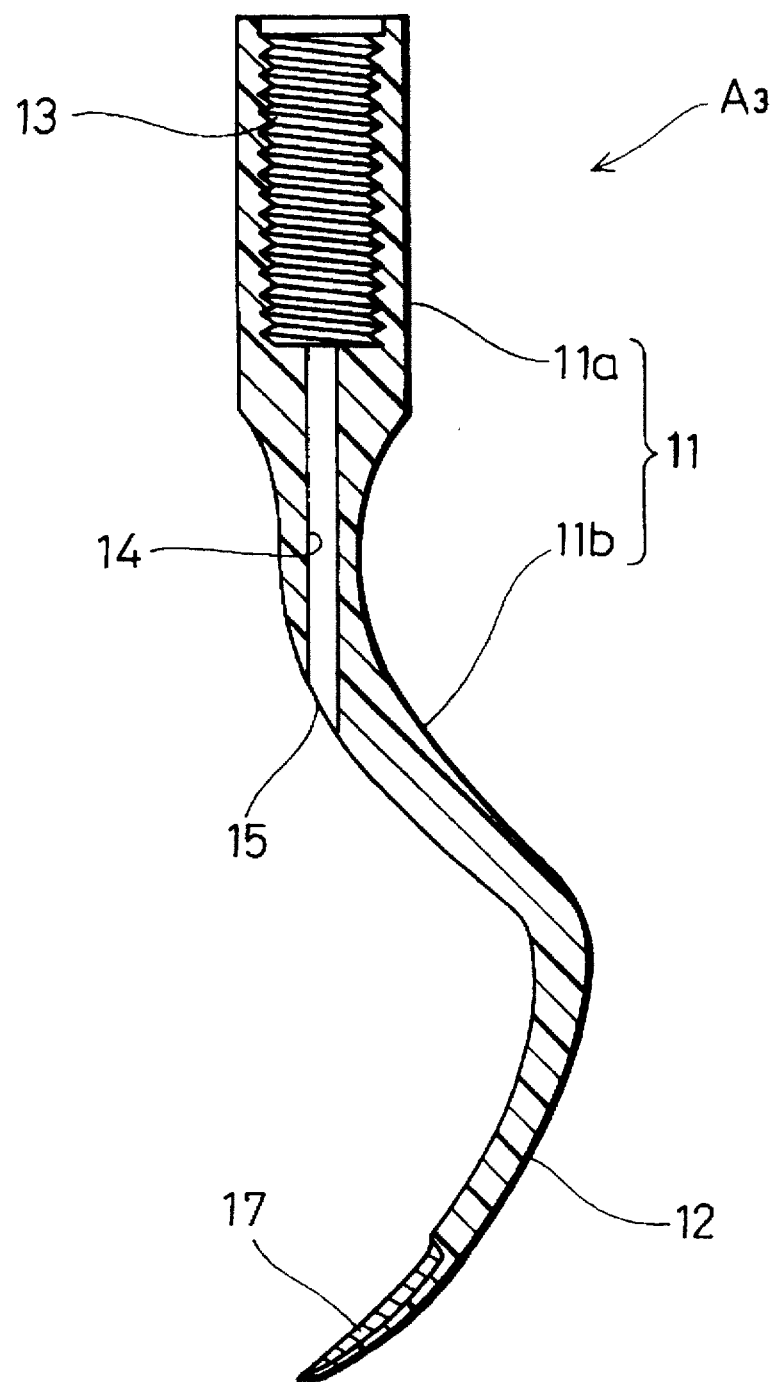
FIG. 5 is a sectional view showing still another dental tip $A_3$ according to the invention.

In order to enhance the grinding effect of the distal end portion of the dental tip, moreover, a grinding portion 17 may be formed at least on part of the distal end portion 12, as in the case of a dental tip $A_3$ shown in FIG. 5.

More specifically, the whole tip may be formed from a composite-material molded product which is composed of a plastic base material and a filler. In this case, a small piece of an abrasive substance is embedded as the grinding portion 17 in part of the distal end. Alternatively, the proximal end portion (connecting portion and support portion) may be formed from a composite-material molded product. In this case, the grinding portion is connected to the support portion so that the distal end portion is replaced by the grinding portion. The grinding used herein includes removing an affected root surface, root canal wall, soft tissue, deposits, etc. and then polishing the cut surface to gloss it.

In this case, the grinding portion to be embedded in the distal end portion must only be formed of a material with a high grinding effect, and is subject to no special restrictions. For example, a metallic, ceramic, or glass piece may be used as the grinding portion.

On the other hand, a needle-shaped file may be used as the grinding portion which replaces the whole distal end portion. A tip having a file on its distal end portion is adapted for use in root canal treatment. The file may be provided with a diamond or the like deposited on its surface. Ensuring a further improved grinding effect, this arrangement is adapted for internal grinding and cleaning of the root canal. In order to obtain an additionally precise polishing effect, the file may be coated with an abrasive plastic material.

The above-described dental tips A can be manufactured in the following manner.

First, the given plastic base material and the filler are mixed in a predetermined ratio, and the resulting mixture or pellets thereof are, for example, injected into a given mold to be molded into an intended shape.

Thus, the dental tips A according to the present invention can be manufactured by directly utilizing the conventional plastic molding technique and apparatus. Once the shape of the mold is settled, therefore, tips having the same shape can be mass-produced by using the same mold, thus ensuring a reduction in cost.

If the metallic member 16 shown in FIG. 4 is set in the mold at the time of the molding operation, the dental tip $A_2$ of the present invention shown in FIG. 4 can be manufactured without embedding the member 16 in the proximal end portion 11.

If the kinds and various specifications of the plastics and fillers and the loading ratios between these materials are fixed without any difference in shape, then any of the dental tips A or composite-material molded products according to the present invention manufactured in the aforementioned manner will be supposed to have a certain hardness and flexural modulus and a fixed natural frequency.

In general, dental tips for clinical use are designed so as to have an optimum shape for an effective treatment of the region to be treated. Usually, therefore, all of practical-use dental tips have the same or substantially the same shapes.

On the other hand, various ultrasonic vibration sources for the dental tips are commercially available. Even though these vibration sources have the same scale, they do not always generate ultrasonic waves of the same oscillation frequency, and to be exact, generates ultrasonic waves of different oscillation frequencies.

In some cases, therefore, the dental tips A of the present invention molded into the optimum shape by using one mold cannot resonate with the optimum oscillation frequency for the type of the ultrasonic vibration source used when they are attached to the ultrasonic scaler for actual use. In these cases, the proximal end portion, for example, of each existing dental tip must be reworked by manual grinding so that it can resonate with the working oscillation frequency.

In changing the shape of the dental tips A, it is generally necessary to fabricate a new mold which conforms to the intended shape. The use of the new mold greatly increases the manufacturing cost of the dental tip, and sometimes cannot make the tip shape optimum for actual use. The aforesaid reworking is also required in this case.

In order to prevent the dental tip from damaging the region to be subjected to dental treatment, it is advisable to lower the output power of the ultrasonic vibration source during the operation of the tip. As the output power is lowered, however, the range of frequencies capable of resonating with the oscillation frequency narrows. If the natural frequencies of the dental tips A formed as the composite-material molded products are deviated from this narrowed range, therefore, the tips A cannot resonate with ease. Thus, even though the output power of the ultrasonic vibration source is low, the dental tips A are positively expected to resonate suitably with the oscillation frequency and produce a satisfactory treatment effect, from the viewpoint of both the effect and safety of the treatment.

In consideration of these problems, according to the present invention, the dental tips A are manufactured by the following method.

Each composite-material molded product, which has the target natural frequency, hardness, and flexural modulus of elasticity, is obtained independently by preparing two composite materials adapted for use in each dental tip A according to the present invention, mixing the materials in a predetermined mixture ratio, and, for example, injection-molding the mixture in a mold with a predetermined shape.

In this case, a plurality of molded products corresponding to varied mixture ratios between the two composite materials are manufactured, the correlations between the mixture ratios and the natural frequency, hardness, and flexural modulus of each obtained molded product are seized by measuring these properties, especially the natural frequency. Based on these correlations, the mixture ratio between the two composite materials is settled.

More specifically, each composite-material molded product is manufactured as follows.

First, a given plastic is mixed with a predetermined quantity of a given filler, whereby two composite materials a and h of different compositions are prepared.

In this case, the composite materials a and b are prepared in the following manner.

The respective compositions of the composite materials a and b are adjusted so that these materials a and b themselves can be used as materials of the dental tip A according to the invention, that is, the respective natural frequencies $f_1$ and $f_2$ of molded products a' and b' which are obtained by injection-molding the composite materials a and b, respectively, can resonate with the oscillation frequency of the ultrasonic vibration source used.

Before manufacturing the intended dental tip A, the following preliminary operations are carried out.

The composite materials a and b are mixed in varied mixture ratios, the resulting mixtures are, for example, injection-molded into molded products of different compositions, and the respective resonance frequencies of the molded products, compared with the optimum oscillation frequency of the ultrasonic vibration source, are measured. The measured resonance frequencies are plotted with respect to the aforesaid mixture ratios to prepare in advance a graph which is indicative of the correlations between the resonance frequencies and the mixture ratios.

Then, the manufacture of the dental tip having the target natural frequency is started. If the natural frequency of the dental tip to be manufactured is $f_n$, the mixture ratio between the composite materials a and b for the resonance frequency $f_n$ is read from the aforesaid graph.

The mixture of the composite materials a and b, mixed in the read mixture ratio, is injected into the mold. Thus, the dental tip A having the predetermined shape and the target natural frequency $f_n$ is formed as a composite-material molded product.

In manufacturing a dental tip with another natural frequency, according to this method, the mold designed for the optimum tip shape is used without change, and the mixture ratio between the two composite materials to be cast is changed. By only doing this, the dental tip having the optimum shape and the target natural frequency can be manufactured with ease. Thus, in manufacturing the dental tip with the target natural frequency, the aforesaid second factor (shape factor) can be ignored. For example, the dental tip with the target natural frequency can be manufactured without changing the design of the mold, so that the manufacturing cost can be reduced considerably.

Thus, each dental tip A is formed of the composite-material molded product which includes the plastic material softer than metal as its matrix and various fillers as reinforcing materials. In conducting periodontal treatment or endodontics by utilizing ultrasonic vibration, therefore, teeth or prostheses can be prevented from being damaged, and calculus or plaque can be restrained from adhering to the surfaces of teeth. Even if the tip shape is complicated, the composite-material molded products can be mass-produced easily and quickly, so that the manufacturing costs of the dental tips A are much lower than those of conventional metallic dental tips. Thus, the dental tips A are disposable, and the possibility of infection with highly infectious diseases, such as serum hepatitis, AIDS, etc., during the treatment can be removed by discarding the tip after using it once in the treatment. Since the base material is formed of plastics, moreover, it can be easily reshaped by shaving after it is molded, so that the tip can enjoy a shape conformable to each individual region in a patient's mouth to be treated.

Since each dental tip A is composed of the composite-material molded product whose hardness and flexural modulus are adjusted within appropriate ranges when it is manufactured, it has a natural frequency such that it can resonate with the oscillation frequency of the ultrasonic vibration source connected thereto. During the dental treatment, therefore, the tip can resonate effectively, thereby producing a satisfactory treatment effect.

In the case of the dental tip A which uses the inorganic filler, in particular, the vibration energy supplied from the ultrasonic vibration source is damped little. Even if the output power of the vibration source is lowered, therefore, effective resonance for the treatment can be induced, so that calculus and other deposits can be removed efficiently. Thus, the tip can be use in the treatment of those regions which are surrounded by the gingiva and cannot be directly viewed from the outside, root branch portions, root surface or apical area under operation, etc. without damaging soft tissue.

In the case of the dental tip A which is compounded with an abrasive substance such as alumina, the abrasive substance, which is uniformly dispersed inside, never fails to exist on the newly exposed surface of the tip even when the tip is ground to change its shape or its surface is worn during actual dental use. Thus, a desired polishing effect can be secured for a long period of time despite the change of the tip shape.

Moreover, the ability of the dental tip A to grind an affected root surface or deposits is improved by forming the grinding portion of an grinding substance on part of the distal end portion. Also, the tip can be used for root canal treatment or the like if the whole distal end portion is replaced by the grinding portion, that is, if the grinding portion is connected to the proximal end portion.

In the dental tips described above, both the proximal end portion (connecting portion and support portion) and the distal end portion are formed of an integral composite-material molded product, or part of the distal end portion is replaced by a file or the like. However, the dental tips according to the present invention are not limited to those embodiments. For example, the connecting portion, support portion, and distal end portion may be manufactured as separate composite-material molded products and joined together. Alternatively, the distal end portion may be joined to, for example, a metallic adapter which serves as the support portion.

The following is a description of dental tips B according to the present invention.

Figure 6:
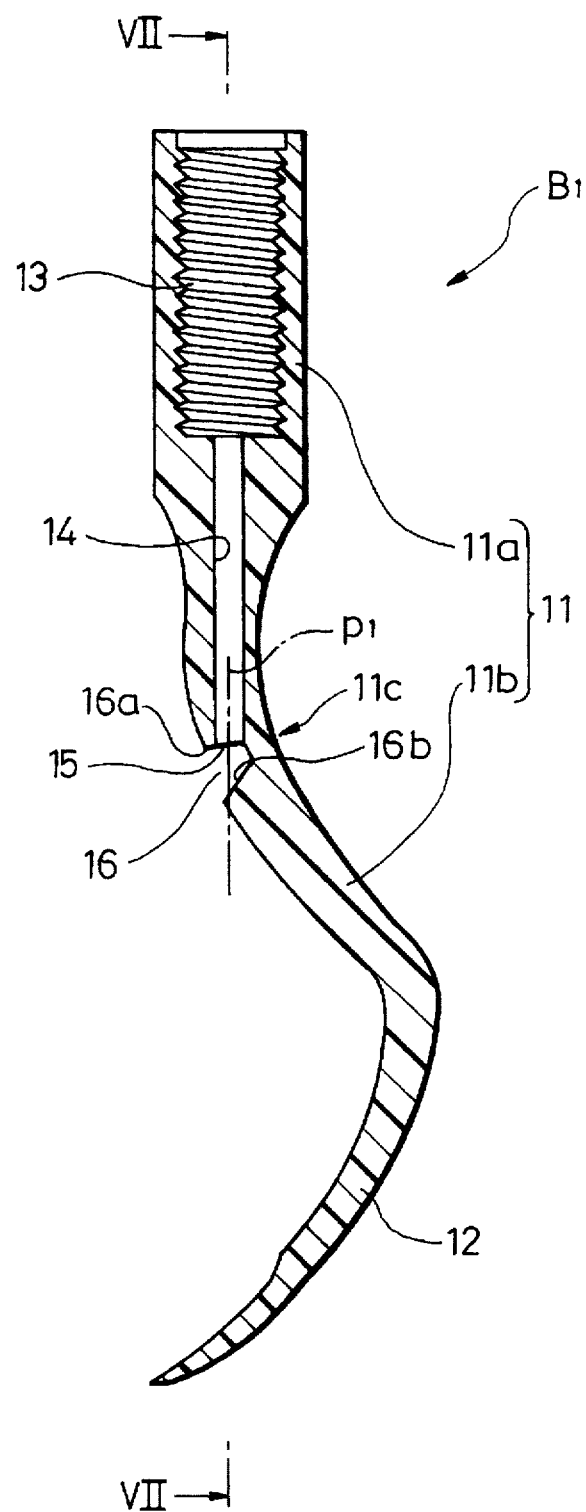
FIG. 6 is a sectional view showing a further dental tip $B_1$ according to the invention.
Figure 7:
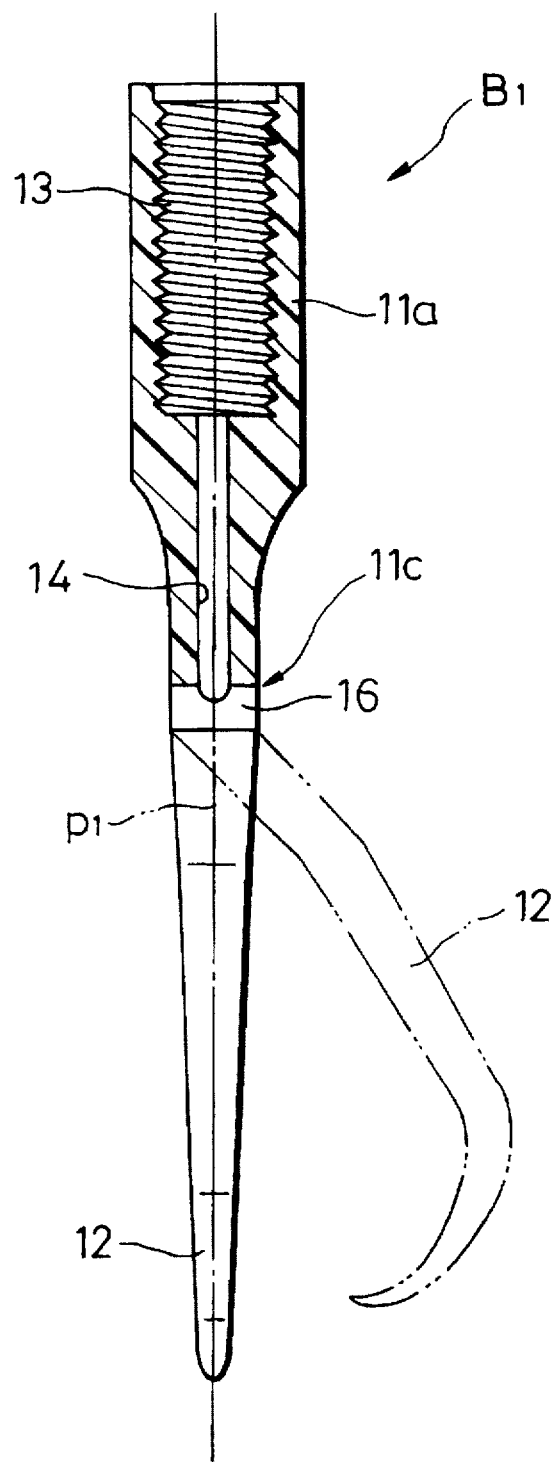
FIG. 7 is a sectional view taken along line VII—VII of FIG. 6.

FIG. 6 is a sectional view showing an example $B_1$ of the dental tips B, and FIG. 7 is a sectional view taken along line VII—VII of FIG. 6.

Except for the arrangement described below, the dental tip $B_1$ has substantially the same shape as the dental tip $A_1$ shown in FIG. 3.

In this dental tip $B_1$, a straight liquid passage 14 is formed extending along an axis $P_1$ of a connecting portion 11a of a proximal end portion 11. One end (upper end) of the passage 14 opens in the bottom of a female screw 13, while the other end is situated between the connecting portion 11a and a support portion 11b, and forms an opening 15 in an intermediate portion 11c which constitutes part of the support portion 11b.

In close vicinity to the opening 15 of the liquid passage 14, a cross groove 16 is formed on the outer wall surface of the intermediate portion 11c so as to extend at right angles to the axis $P_1$. It is necessary only that the cross groove 16 be situated in a position such that some (preferably almost all) of irrigating water or the like ejected from the opening 15 can run against it. Preferably, the opening 15 should be designed so that it opens in a side wall surface (upper wall surface) 16a of the cross groove 16 and that the axis $P_1$ crosses the other side wall surface (lower wall surface) 16b of the groove 16.

Thus, in consideration of the ease of formation of a film which will be mentioned later, it is advisable to situate the cross groove 16 so that the groove 16 and the axis $P_1$ of the liquid passage 14 extend at right angles to each other. Alternatively, however, the groove 16 may be inclined at a narrow angle such that it cannot exert a bad influence upon the vibration characteristics of a distal end portion 12.

The tip which resonates with the ultrasonic vibration supplied from the ultrasonic vibration source exhibits a maximum amplitude at its distal end. In the case where a liquid film is formed at the distal end of the tip, liquid drops from the film are scattered from the tip end. Thus, if a film of the liquid jetted from the opening 15 is formed on the outer surface of the distal end portion 12 of the tip, the liquid ejected by the dispersive force and surface tension of the liquid drops can be allowed to reach the distal end portion 12.

In this dental tip $B_1$, the cross groove 16 is formed in the vicinity of the opening 15 so as to extend substantially at right angles to the axis $P_1$ of the liquid passage 14. In this arrangement, the liquid jetted from the opening 15 can run against the cross groove 16 so that its jetting speed is reduced. Thus, the aforesaid liquid film can be formed on the outer surface of the tip without causing the liquid to leave the tip surface.

Although the sectional shape of the cross groove 16 is not subject to any restriction, it should preferably be U-shaped, as shown in FIG. 6.

The opening 15 need not always open in the side wall surface 16a of the cross groove 16, and the liquid passage axis $P_1$ need not cross the side wall surface 16b of the groove 16 which faces the opening 15. In the case of the preferred shape shown in FIGS. 6 and 7, however, the opening 15 opens in the side wall surface 16a of the cross groove 16, and the passage axis $P_1$ crosses the side wall surface 16b of the groove 16 which faces the opening 15. If the cross groove 16 and the opening 15 are relatively positioned in this manner, most of the irrigating water jetted from the opening 15 can be caused to run against the side wall surface 16b of the groove 16 so that its jetting speed is reduced. Thus, the ejected irrigating water overflows the cross groove 16 and forms a liquid film which covers the outer wall surface of the intermediate portion 11c. Even when the tip $B_1$ is used with its distal end portion 12 upward, according to this arrangement, the liquid film allows the irrigating water to reach the distal end portion 12 via the intermediate portion 11c.

Figure 8:
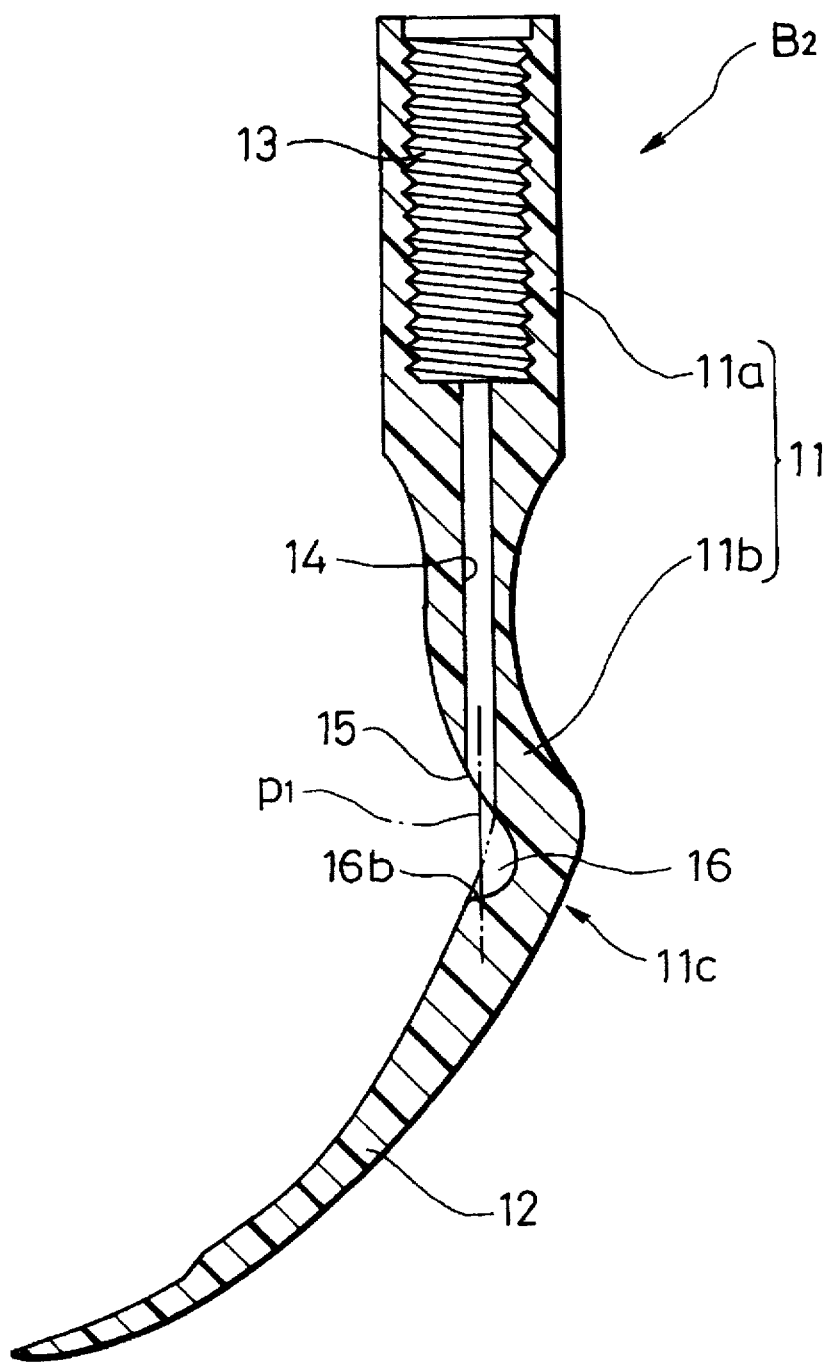
FIG. 8 is a sectional view showing another dental tip $B_2$ according to the invention.

FIG. 8 is a sectional view showing another example $B_2$ of the dental tips B according to the present invention.

The dental tip $B_2$, unlike the dental tip $B_1$ shown in FIGS. 6 and 7, is designed so that the opening 15 of the liquid passage 14 in the proximal end portion 11 opens in the outer wall surface of the intermediate portion 11c, and the cross groove 16 is formed under the opening 15. Since the intermediate portion 11c is curved, the opening 15 is opposed to the side wall surface (lower wall surface) 16b of the groove 16. Preferably, in this case, the liquid passage axis $P_1$ should cross the side wall surface 16b. Also with this positional relationship, most of the irrigating water jetted from the opening 15 can be caused to run against the side wall surface 16b of the groove 16 so that its jetting speed is reduced. Thus, the ejected irrigating water or the like overflows the cross groove 16 and forms a liquid film which covers the outer wall surface of the intermediate portion 11c. This liquid film allows the irrigating water or the like to reach the distal end portion 12 via the intermediate portion 11c.

In the cases of the dental tips $B_1$ and $B_2$, the single cross groove 16 is formed near the opening 15. Alternatively, however, a plurality of cross grooves may be formed extending parallel to the groove 16, on the distal end side of the tip. These additional cross grooves can be filled with the irrigating water or the like ejected from the opening 15, so that a better liquid film can be formed on the outer wall surface of the tip.

Figure 9:
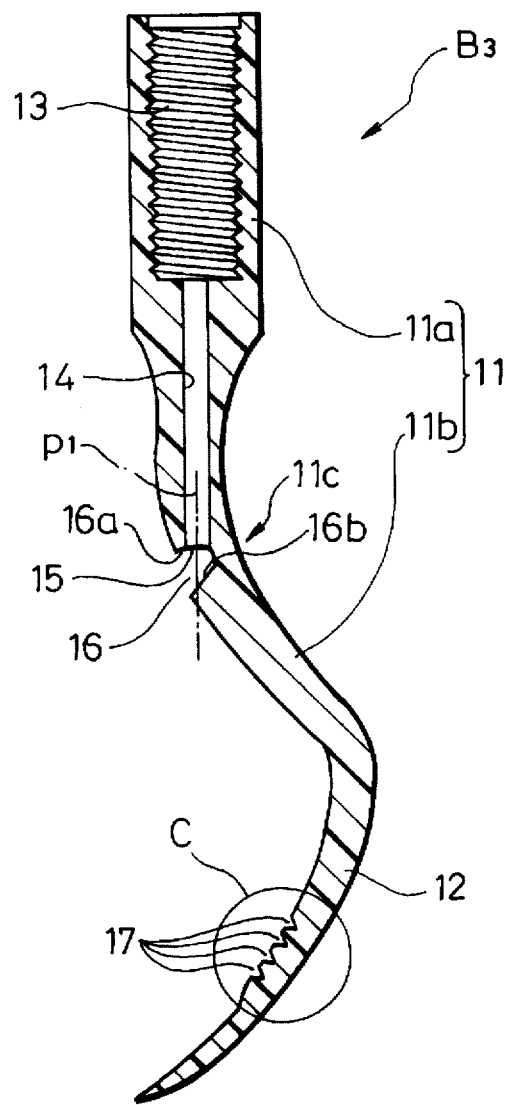
FIG. 9 is a sectional view showing still another dental tip $B_3$ according to the invention.
Figure 10:
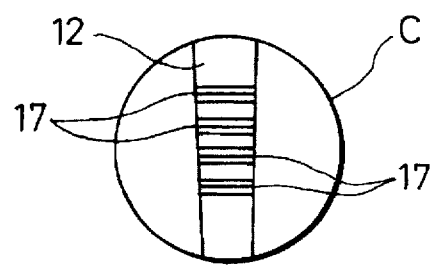
FIG. 10 is a partial enlarged view of a region C in FIG. 9.

The more the distal end portion 12 is deviated crosswise in the groove forming direction with respect to the opening 15, moreover, the more difficult the transfer of the irrigating water or the like to the distal end portion will be. In the case where the tip is actually used with the distal end portion 12 upward, in particular, the irrigating water or the like sometimes cannot reach the distal end. FIG. 9 and FIG. 10 (enlarged view of a region C of FIG. 9) show a dental tip $B_3$ which can cope with this problem. The tip $B_3$ is formed with a plurality (suitable number) of auxiliary cross grooves 17 which are situated in a suitable position at the distal end portion 12, preferably in a position to which the irrigating water or the like can be transferred, and extend parallel to the cross groove 16. These auxiliary cross grooves 17 serve to receive the irrigating water delivered thereto and allow it to collect therein. Thus, the irrigating water collected by creeping can be caused to reach the distal end portion of the tip.

Preferably, the auxiliary cross grooves 17 are formed on the outer surface of the tip which faces the opening 15, so as to extend at right angles to the extending direction of the distal end portion 12 (or parallel to the cross groove 16). Alternatively, however, the auxiliary grooves 17 may be formed on the other side of the outer surface of the intermediate portion 11c with respect to the cross groove 16.

In the case of each dental tip B, the cross groove 16 is formed in the vicinity of the opening 15. In this case, the dental tip may be one formed of the composite-material molded product according to the present invention or a conventional metallic one.

[EXAMPLE 1]

A composite-material molded product having the shape shown in FIG. 3 was manufactured by kneading 70% by weight of polyphenylene sulfide and 30% by weight of a carbon fiber with the filament diameter of 8 μm and aspect ratio of 15 to 100 into pellets, and injection- molding the resulting pellets.

The obtained composite-material molded product is an integral molded product which measures 36.3 mm in overall length. The distal end portion 12 is bent twice in the regions $a_1$ and $a_2$, and is designed so that it can efficiently grind and remove calculus and other deposits, which adhere to complicated regions in the mouth, during dental treatment, and can satisfactorily resonate when connected to the ultrasonic vibration source. A screw portion is provided between the tip and the ultrasonic vibration source.

Figure 1:
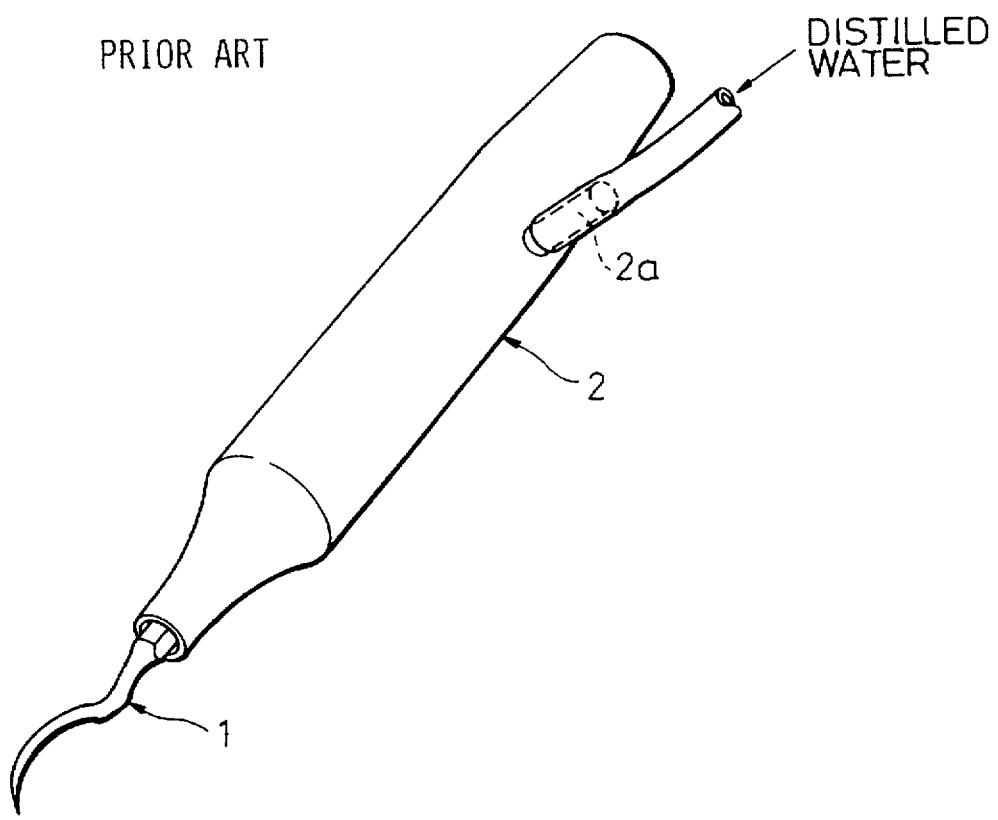
FIG. 1 is a perspective view showing a dental tip attached to a hand piece of an ultrasonic scaler.

Then, the composite-material molded product was attached as a dental tip to the hand piece 2, as shown in FIG. 1, and the hand piece 2 was actuated.

The ultrasonic vibration source which is contained in the hand piece 2 oscillates with power of 0.1 to 10 W, and the optimum value and allowance of its oscillation frequency are settled to 31 kHz and ±2 kHz, respectively.

The tip resonated with a frequency of 32.8±0.3 kHz.

When the dental treatment was conducted in this state, the resulting tip displayed a performance lower than that of the conventional metallic dental tip but clinically feasible, with lower output power. No teeth or prostheses suffered any special damage.

A specimen for specific measurement was prepared using the same materials of the composite-material molded product having the aforesaid shape, and its hardness (Rockwell hardness; M scale) and flexural modulus of elasticity measured 104 and 20,000 MPa, respectively.

[EXAMPLE 2]

A dental tip having the shape shown in FIG. 3 was manufactured in the same manner as Example 1 except that a composite-material molded product was prepared by using 70% by weight of polyphenylene sulfide and 30% by weight of a carbon fiber with the filament diameter of 8 μm and aspect ratio of 15 to 100, that the metallic member (stainless steel) 16 was embedded in the connecting portion 11a, as shown in FIG. 4, in order to make the state of connection with the ultrasonic vibration source better, thereby improving the ultrasonic vibration transfer efficiency, and that the female screw 13 was formed on the inner surface of the member 16. The dental tip was actuated in the same conditions.

The tip resonated with a frequency of 30.6±0.3 kHz.

When the dental treatment was conducted in this state, the resulting tip displayed a performance higher than that of Example 1 and equivalent to that of the conventional metallic dental tip, even with lower output power (3W). In processes of actual use, no teeth or prostheses suffered any damage.

[EXAMPLE 3]

A composite-material molded product having the shape shown in FIG. 3 was manufactured by kneading 60% by weight of polyphenylene sulfide and 40% by weight of fibrous potassium titanate with the filament diameter of 0.3 to 0.6 μm and aspect ratio of 15 to 67 into pellets, and injection-molding the resulting pellets.

This composite-material molded product was attached to the hand piece 2 in the same manner as in Example 1, and was actuated as a dental tip.

The tip resonated with a frequency of 30.4±0.3 kHz.

When the dental treatment was conducted in this state, the resulting tip displayed a performance higher than that of Example 1 and equivalent to that of the conventional metallic dental tip, even with lower output power (1 to 2W). In processes of actual use, no teeth or prostheses suffered any damage. When the hand piece 2 was screwed tight, the tip was liable to crack and fracture at the junction.

A specimen for specific measurement was prepared using the same materials of the composite-material molded product having the aforesaid shape, and its hardness (Rockwell hardness; M scale) and flexural modulus of elasticity measured 104 and 14,000 MPa, respectively.

[EXAMPLE 4]

A composite-material molded product having the shape shown in FIG. 3 was manufactured using pellets prepared by kneading 60% by weight of polyphenylene sulfide, 30% by weight of a carbon fiber with the filament diameter of 8 μm and aspect ratio of 15 to 100, and 10% by weight of fibrous potassium titanate with the filament diameter of 0.3 to 0.6 μm and aspect ratio of 15 to 67. This molded product was actuated in the same conditions. The tip resonated with a frequency of 32.8±0.3 kHz.

When the dental treatment was conducted in this state, the resulting tip displayed a performance higher than that of Example 1 and equivalent to those of Example 3 and the conventional metallic dental tip. In processes of actual use, no teeth or prostheses suffered any damage. Cracking and the like at the threaded junction, which may be caused in the case of Example 3, became less liable to occur.

A specimen for specific measurement was prepared using the same materials of the composite-material molded product having the aforesaid shape, and its hardness (Rockwell hardness; M scale) and flexural modulus of elasticity measured 94 and 25,000 MPa, respectively.

[EXAMPLE 5]

A composite-material molded product having the shape shown in FIG. 3 was manufactured using pellets prepared by mixing 60% by weight of polyphenylene sulfide 30% by weight of a carbon fiber with the filament diameter of 8 μm and aspect ratio of 15 to 100, 10% by weight of a fibrous potassium titanate with the filament diameter of 0.3 to 0.6 μm and aspect ratio of 15 to 67, and kneading the mixture together with 20% by volume of alumina powder with the particle size of 1 to 25 μm. This molded product was actuated as a dental tip in the same conditions of Example 1.

The tip resonated with a frequency of 32.1±0.3 kHz.

When the dental treatment was conducted in this state, the resulting tip displayed a performance equivalent to that of the conventional metallic dental tip and particularly high polishing capability. This polishing capability lasted long, and a satisfactory treatment effect was produced even with lowered output power of 0.3 W.

However, no teeth or prostheses suffered any special damage, since alumina was dispersed so well that every part of the tip was able to produce the same polishing effect. Internal observation of the tip surface by means of an electron microscope indicated that alumina was dispersed uniformly in any part of the tip.

[EXAMPLE 6]

The dental tip $A_3$ shown in FIG. 5 was manufactured by embedding the metallic piece (stainless steel) 17 in the distal end portion of the composite-material molded product of Example 4.

This dental tip was actuated in the same conditions of Example 1.

The tip resonated with a frequency of 31.8±0.3 kHz.

When the dental treatment was conducted in this state, the resulting tip displayed a performance equivalent to that of the conventional metallic dental tip and much higher polishing capability than Example 4.

[EXAMPLE 7]

A composite-material molded product having the shape shown in FIG. 3 was manufactured by kneading 80% by weight of polyacetal and 20% by weight of a carbon fiber with the filament diameter of 8 μm and aspect ratio of 15 to 100 into pellets, and injection-molding the resulting pellets.

This composite-material molded product was attached as a dental tip to the hand piece used in Example 1, and was actuated. The resonating performance was lower than in Examples 3 and 4.

The tip did not resonate with the output power of 0.3 W, in particular. When the output power was increased to 8 W, the distal end portion fractured.

When the output power was adjusted to 3 W, the tip somehow resonated with a frequency of 30.9±0.3 kHz, although not in a satisfactory state for treatment.

When the dental treatment was conducted in this state, the resulting tip failed to display a performance equivalent to that of the conventional metallic dental tip. Although no teeth or prostheses suffered any damage in processes of actual use, a satisfactory effect for treatment was not obtained.

A specimen for specific measurement was prepared using the same materials of the composite-material molded product having the aforesaid shape, and its hardness (Rockwell hardness; M scale) and flexural modulus of elasticity measured 78 and 5,600 MPa, respectively.

[EXAMPLE 8]

A composite-material molded product having the shape shown in FIG. 3 was manufactured by kneading 60% by weight of polyphenylene sulfide, 35% by weight of fibrous potassium titanate, and 5% by weight of an aramide fiber with the filament diameter of 12 μm into pellets, and injection-molding the resulting pellets.

This composite-material molded product was attached as a dental tip to the hand piece used in Example 1, and was actuated. Although the tip did not resonate with the output power of 1 W, it resonated with a frequency of 31.5±0.3 kHz when the output power was increased.

When the dental treatment was conducted in this state, the performance of the resulting tip was found to be lower than that of the tip of Example 3. However, this tip felt softer and smoother than the tip of Example 3 and even when the output power of the ultrasonic vibration source was increased, no teeth or prostheses suffered any damage.

A specimen for specific measurement was prepared using the same materials of the composite-material molded product having the aforesaid shape, and its hardness (Rockwell hardness; M scale) and flexural modulus of elasticity measured 75 and 7,200 MPa, respectively.

[EXAMPLE 9]

The composite material a was prepared by mixing 60% by weight of polyphenylene sulfide with 40% by weight of fibrous potassium titanate with the average filament diameter of 0.3 to 0.6 μm and aspect ratio of 15 to 67.

Also, composite material h was prepared by mixing 60% by weight of polyphenylene sulfide with 30% by weight of a carbon fiber with the average filament diameter of 8 μm and aspect ratio of 15 to 100 and 10% by weight of fibrous potassium titanate with the average filament diameter of 0.3 to 0.6 μm and aspect ratio of 15 to 67.

The composite materials a and b in varied mixture ratios were injection-molded in a mold, whereupon 20 dental tips having the shape shown in FIG. 3 were produced.

Figure 11:
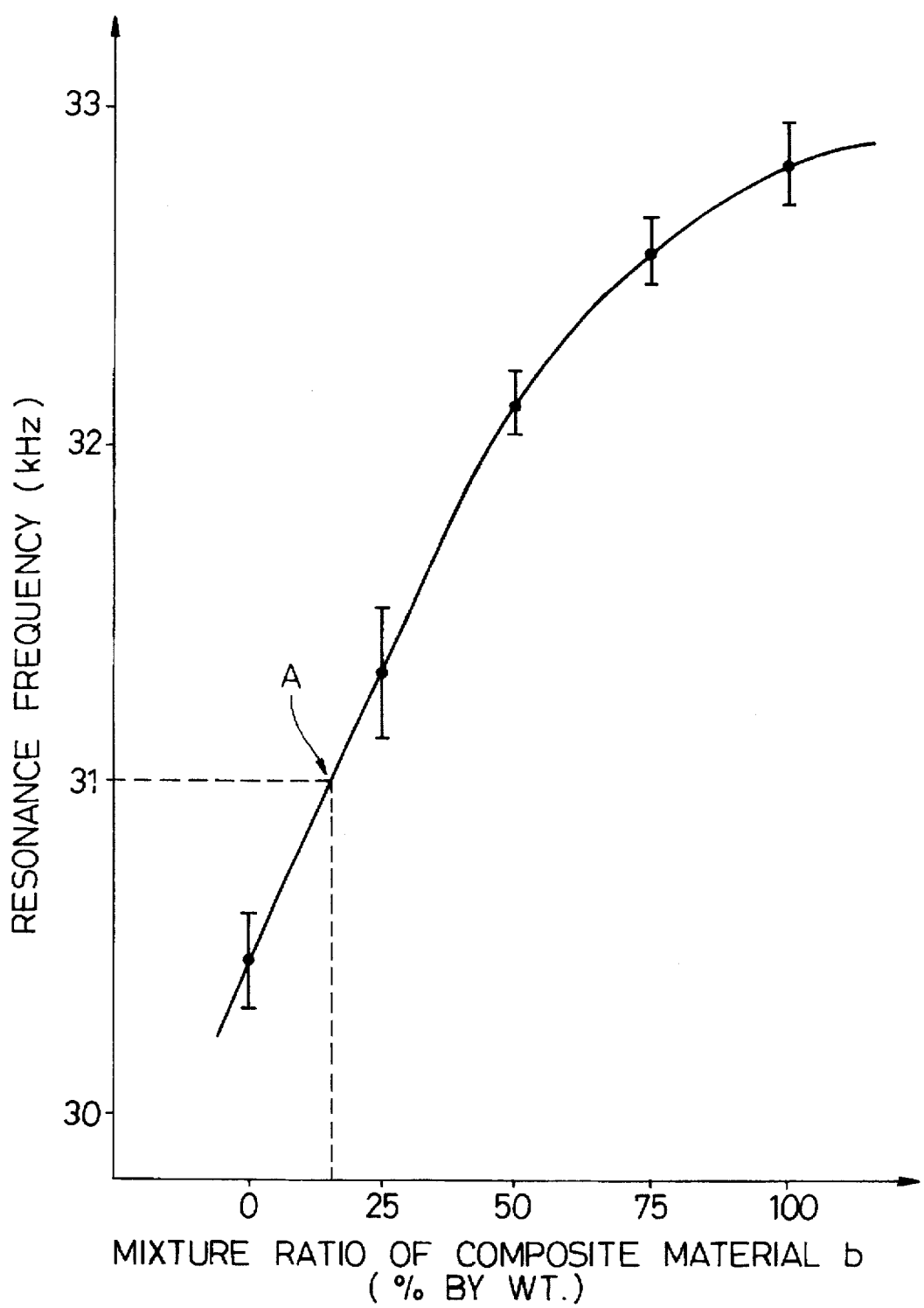
FIG. 11 is a graph illustrating the relationship between the mixture ratio between two composite materials a and b used as materials of the molded product shown in FIG. 3 and the natural frequency of the molded product.

The respective resonance frequencies $f_n$ of the individual dental tips were measured, and their average values and standard deviations were obtained. Table 1 and FIG. 11 show the results of the measurement.

TABLE 1

|  | Resonance Frequency (kHz) | |
| --- | --- | --- |
|  | Average | Standard deviation |
| Composite material a only (composite material b: 0% by weight) | 30.45 | ±0.15 |
| 25% composite material b by weight (composite material a: 75% by weight) | 31.32 | ±0.20 |
| 50% composite material b by weight (composite material a: 50% by weight) | 32.12 | ±0.09 |
| 75% composite material b by weight (composite material a: 25% by weight) | 32.58 | ±0.09 |
| Composite material b only (composite material a: 0% by weight) | 32.83 | ±0.13 |

Figure 12:
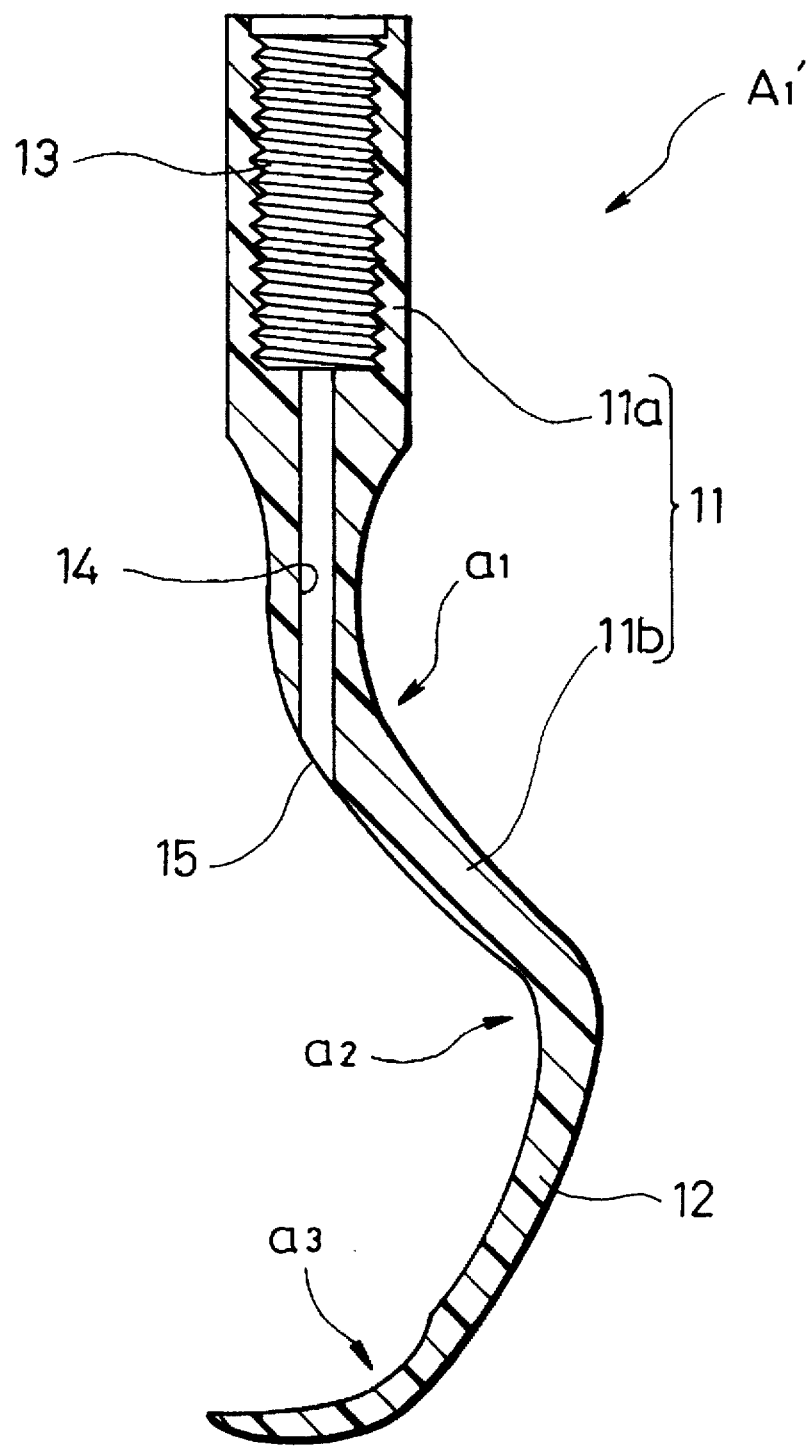
FIG. 12 is a sectional view showing another dental tip $A_1'$ according to the invention.

Twenty composite-material molded products $A_1'$ having the shape shown in FIG. 12 were manufactured as dental tips, varying the mixture ratios between the composite materials a and b. Each molded product $A_1'$ has an overall length of 34.1 mm, and its distal end portion 12 are bent in three regions $a_1$, $a_2$ and $a_3$.

The respective resonance frequencies $f_n$ of the individual dental tips were measured, and their average values and standard deviations were obtained. Table 2 and FIG. 12 show the results of the measurement.

TABLE 2

|  | Resonance Frequency (kHz) | |
| --- | --- | --- |
|  | Average | Standard deviation |
| Composite material a only (composite material b: 0% by weight) | 28.92 | ±0.17 |
| 25% composite material b by weight (composite material a: 75% by weight) | 30.20 | ±0.21 |
| 50% composite material b by weight (composite material a: 50% by weight) | 30.96 | ±0.07 |

TABLE 2-continued

|  | Resonance Frequency (kHz) | |
| --- | --- | --- |
|  | Average | Standard deviation |
| 75% composite material b by weight (composite material a: 25% by weight) | 31.54 | ±0.09 |
| Composite material b only (composite material a: 0% by weight) | 31.85 | ±0.17 |

As is evident from the above results, the composite-material molded products $A_1$ and $A_1'$ have different resonance frequencies despite the same composition.

Based on the results shown in Table 1 and FIG. 11, a point A on the curve of FIG. 11 at which the resonance frequency is 31 kHz was obtained, and the mixture ratio corresponding to the point A was read. The read value for the composite material b is 15% by weight compared with 85% by weight for the composite material a.

Then, injection molding was carried out so that the aforesaid mixture ratio was obtained between the composite materials a and b, whereupon dental tips having the shape shown in FIG. 3 were produced.

When the respective resonance frequencies of the dental tips were measured, an average value of 31.08 kHz and standard deviation of ±0.21 kHz were obtained. Thus, the difference from the target resonance frequency was 0.08 kHz on the average.

Based on the results shown in Table 2 and FIG. 13, dental tips with a natural frequency of 31 kHz was manufactured as follows.

Figure 13:
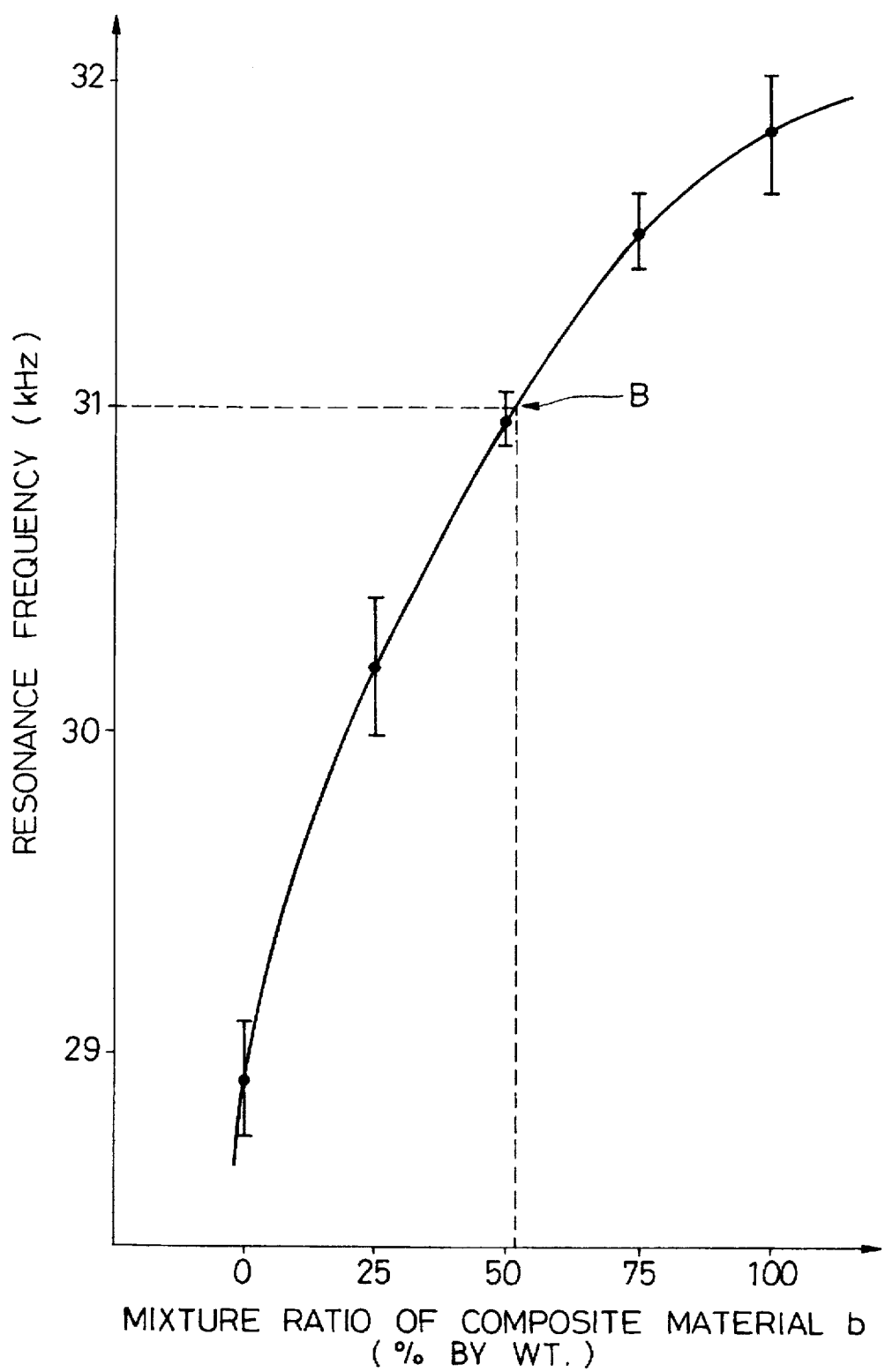
FIG. 13 is a graph illustrating the relationship between the mixture ratio between the composite materials a and b used as materials of the molded product shown in FIG. 12 and the natural frequency of the molded product.

First, a point B on the curve of FIG. 13 at which the resonance frequency is 31 kHz was obtained, and the mixture ratio corresponding to the point B was read. The read value for the composite material b is 52.5% by weight compared with 47.5% by weight for the composite material a.

Then, injection molding was carried out so that the aforesaid mixture ratio was obtained between the composite materials a and b, whereupon dental tips having the shape shown in FIG. 12 were produced.

When the respective resonance frequencies of the dental tips were measured, an average value of 30.97 kHz and standard deviation of ±0.26 kHz were obtained. Thus, the difference from the target resonance frequency was 0.03 kHz on the average.

[EXAMPLE 10]

Figure 14:
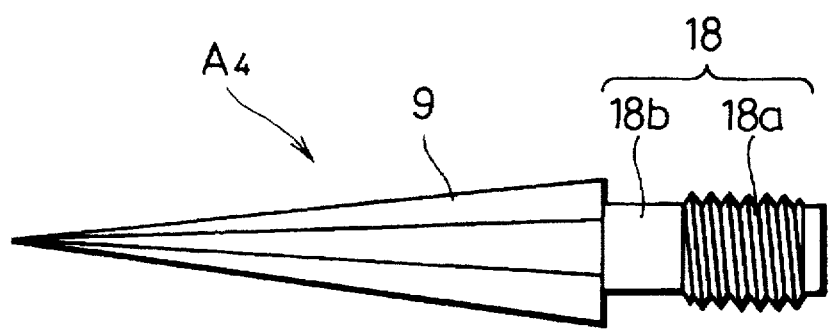
FIG. 14 is a side view showing a dental rotating tip $A_4$ according to the invention.

FIG. 14 is a side view showing a dental rotating tip according to the present invention which is used in a rotosonic scaler. This dental rotating tip $A_4$ has the same shape as the conventional metallic rotating tip for rotosonic dental treatment, and is composed of a proximal end portion 18, which includes a connecting portion 18a connected to the rotosonic scaler and a support portion 18b, and a distal end portion 19 in the form of a hexagonal pyramid.

Thus, the dental rotating tip $A_4$ according to the invention, which has the same shape as the conventional metallic tip for rotosonic scaler, can be attached directly to a conventional apparatus.

The dental rotating tip $A_4$ is formed from a composite-material molded product having the same composition as Example 4.

Preferably, the composite-material molded product as the material of the dental rotating tip for rotosonic scaler has an appropriate hardness such that it can effectively remove calculus and other deposits without damaging the affected region to treated. More specifically, the hardness of the composite-material molded product for the dental rotating tip should preferably be adjusted to 90 or more in terms of the Rockwell hardness (M scale) so that calculus and the like can be removed by grinding without damaging the surfaces of teeth or prostheses, as in the case of Example 1.

Also in this example, the same materials of Example 1 can be used in the form of a combination of a plastic base material and a filler when the composite-material molded product is manufactured.

This rotating tip for dental treatment can be attached to the rotosonic scaler in the same manner as the conventional metallic tip.

The rotating tip according to the present invention, like the conventional metallic tip, can be used for dental treatment, and can minimize the possibility of damaging teeth or prostheses while maintaining its calculus removing capability equivalent to that of the conventional metallic tip.

[EXAMPLE 11]

Figure 15:
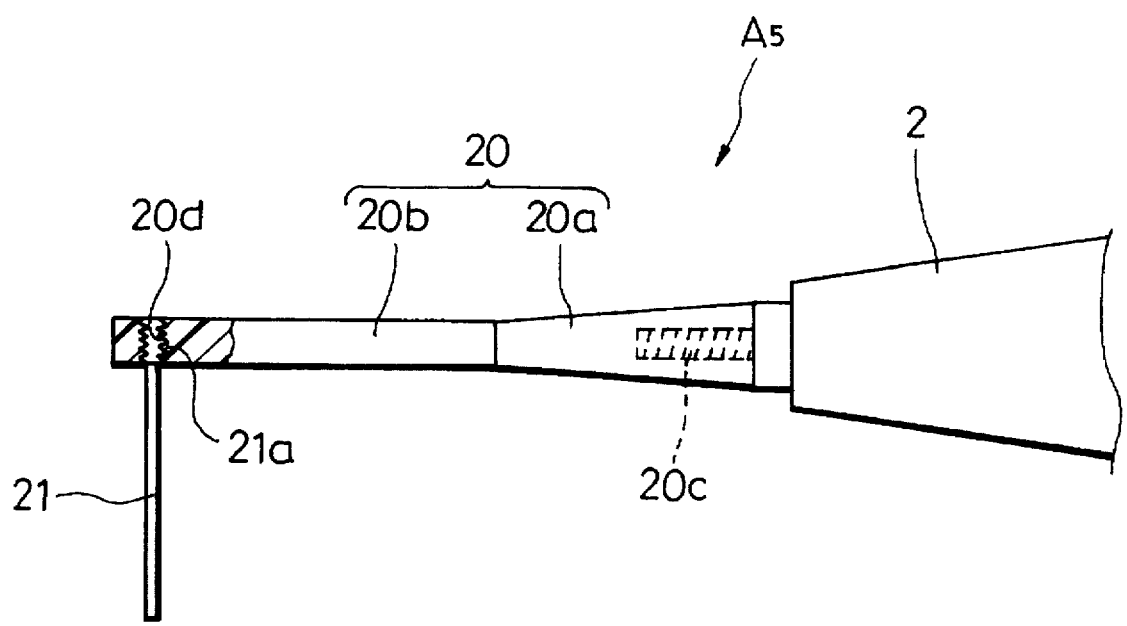
FIG. 15 is a side view showing a dental tip $A_5$ for root canal treatment according to the invention.

FIG. 15 shows a dental tip according to the present invention which is used for root canal treatment. This dental tip $A_5$ is composed of a proximal end portion 20 and a file 21 as a grinding portion. The proximal end portion 20 includes a connecting portion 20a connected to an ultrasonic vibration source of an ultrasonic scaler and a support portion 20b which supports the file 21. The connecting portion 20a is formed with a screw portion 20c, to which the ultrasonic scaler is connected. Diamond is deposited on the surface of the file 21 by vapor deposition.

In manufacturing the dental tip $A_5$, the proximal end portion 20 having the aforesaid shape is first formed as a composite-material molded product in the same manner as in each of the foregoing examples, and the file 21 is then connected to the distal end of the support portion 20. Thus, in this molded product, the support portion 20b serves also as the distal end portion according to the present invention.

Preferably, the file 21 is connected in a manner such that a male screw 21a formed on the basal part of the file 21 is screwed into a female screw 20d formed in the distal end of the support portion (distal end portion) 20b. Alternatively, the file 21 may be heated to be fused to the support portion 20b.

This dental tip $A_5$ is attached to the ultrasonic vibration source of the ultrasonic scaler when it is used for root canal treatment, and produces specially good effects in root canal enlargement, cleaning, irrigating, etc., and reversed root canal treatment during operation.

Since the dental tip $A_5$ is formed by injection-molding the composite-material molded product, it can be manufactured relatively easily, and the metallic part of the distal file can be incorporated integrally in the tip during the injection molding operation. Thus, the tip $A_5$ can be manufactured at lower cost than the conventional metallic tip, and can be used a disposable article.

Figure 16:
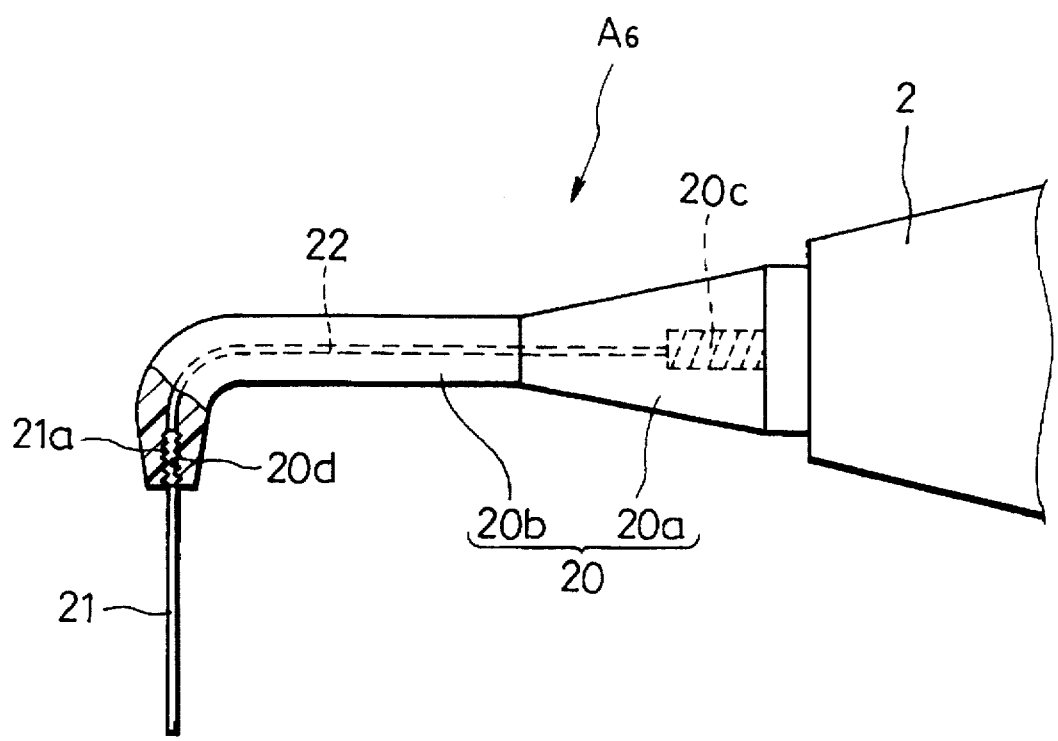
FIG. 16 is a side view showing another dental tip $A_6$ for root canal treatment according to the invention.

During the manufacture of the tip of this type, the distal end of the support portion (distal end portion) 20b may be bent in the manner shown in FIG. 16. This tip $A_6$ for root canal treatment is formed inside with a passage 22 which extends from the screw portion 20c to the support portion 20b, and the file 21 is connected to the distal end of the support portion 20b.

In the case of this tip $A_6$, irrigating water (or chemical agent) can be jetted against the file 21 from the passage 22.

What is claimed is:

1. A dental tip comprising:
   a curved distal end portion adapted to act on a region to be subjected to dental treatment; and
   a proximal end portion adapted to be connected to a drive source,
   said distal and proximal end portions being made of a molded composite-material comprising a plastic base material and at least one of an inorganic filler and an organic filler compounded therewith.

2. A dental tip according to claim 1, wherein the drive source is an ultrasonic vibration source, wherein said molded composite-material has a characteristic natural frequency whereby said molded composite-material resonates in the vicinity of an oscillation frequency of the ultrasonic vibration source.

3. A dental tip according to claim 1, wherein said molded composite-material has a Rockwell hardness (M scale) between 65 to 120 and a flexural modulus of elasticity between 2,500 to 25,000 Mpa.

4. A dental tip according to claim 1, wherein said plastic base material is selected from the group consisting of polyphenylene sulfide, polyamide, polyethylene terephthalate, polybutylene terephthalate, liquid crystal polymer, polycarbonate, polyether-ether ketone, polyether ketone, polyether sulfone, polysulfone, polyetherimide, polyamideimide, polyimide, and polyacetal.

5. A dental tip according to claim 4, wherein said plastic base material is polyphenylene sulfide.

6. A dental tip according to claim 1, wherein said inorganic filler is selected from the group consisting of carbon fiber, fibrous potassium titanate, glass fiber, alumina fiber, titanium oxide, boron, and talc.

7. A dental tip according to claim 6, wherein said inorganic filler is at least one of carbon fiber and fibrous potassium titanate.

8. A dental tip according to claim 1, wherein said organic filler is an aramide (aromatic polyamide) fiber.

9. A dental tip according to claim 1, wherein said molded composite-material is composed of 50 to 90% by weight of polyphenylene sulfide and 10 to 50% by weight of at least one of carbon fiber and fibrous potassium titanate.

10. A dental tip according to claim 1, wherein said molded composite-material is further compounded with an abrasive substance.

11. A dental tip according to claim 10, wherein said abrasive substance is selected from the group consisting of alumina, silica, glass, zirconia, silicon carbide, boron carbide, and diamond.

12. A dental tip according to claim 11, wherein said said abrasive substance is alumina.

13. A dental tip according to claim 1, wherein at least part of a surface of said distal end portion is provided with an abrasive substance, thereby forming a grinding portion.

14. A dental tip according to claim 13, wherein said grinding portion is a file.

15. A dental tip according to claim 13, wherein said abrasive substance is selected from the group consisting of metallic, ceramic, and glass pieces.

16. A dental tip according to claim 1, wherein an interface portion of said proximal end portion adapted to be connected to the drive source is one of an embedded metallic material portion having a female screw thread, a female screw thread plated with a metallic material, and a metal band adapted to bind said proximal end portion and the drive source.

17. A dental tip according to claim 1, wherein said proximal end portion is provided with a liquid passage extending therethrough along an axis of said proximal end portion.

18. A dental tip comprising:
- a distal end portion having a desired curved shape and adapted to act on a region to be subjected to dental treatment;
- a proximal end portion adapted to be connected to a drive source;
- a liquid passage opening onto an intermediate portion between the distal and proximal end portions; and
- a transverse cross groove adjacent said opening of said liquid passage and extending substantially at right angles to an axis of said liquid passage, said distal and proximal end portions being made of a molded composite-material comprising a plastic base material and at least one of an inorganic filler and an organic filler compounded therewith.

19. A dental tip according to claim 18, wherein said opening opens in a side wall surface of the cross groove.

20. A dental tip according to claim 18, wherein the liquid passage axis of said opening intersect a side wall surface of the cross groove on which the opening faces.

21. A dental tip according to claim 18, wherein said distal end portion terminates at a point.

* * * * *